(12) United States Patent
Geiss et al.

(10) Patent No.: US 9,206,412 B2
(45) Date of Patent: Dec. 8, 2015

(54) THIOXOTHIAZOLIDINE INHIBITORS

(71) Applicants: Colorado State University Research Foundation, Fort Collins, CO (US); State of Colorado acting by and on behalf of the Board of Trustees of the University of Northern Colorado, Greeley, CO (US)

(72) Inventors: Brian J. Geiss, Fort Collins, CO (US); Susan M. Keenan, Lyons, CO (US); Hillary Jo Beek, Douglas, WY (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 13/907,485

(22) Filed: May 31, 2013

(65) Prior Publication Data

US 2014/0004590 A1    Jan. 2, 2014

Related U.S. Application Data

(60) Provisional application No. 61/653,559, filed on May 31, 2012.

(51) Int. Cl.
| | | |
|---|---|---|
| *A61K 31/425* | (2006.01) | |
| *C12N 9/99* | (2006.01) | |
| *C12N 7/00* | (2006.01) | |
| *C12N 9/12* | (2006.01) | |
| *A61K 31/426* | (2006.01) | |
| *A61K 9/00* | (2006.01) | |
| *A61K 9/06* | (2006.01) | |
| *A61K 9/20* | (2006.01) | |

(Continued)

(52) U.S. Cl.
CPC . *C12N 9/99* (2013.01); *A61K 9/008* (2013.01); *A61K 9/0014* (2013.01); *A61K 9/0019* (2013.01); *A61K 9/06* (2013.01); *A61K 9/2018* (2013.01); *A61K 9/2054* (2013.01); *A61K 9/4858* (2013.01); *A61K 9/4866* (2013.01); *A61K 31/426* (2013.01); *C12N 7/00* (2013.01); *C12N 9/1241* (2013.01); *A61K 31/427* (2013.01); *C12N 2770/24122* (2013.01)

(58) Field of Classification Search
CPC .................................................. A61K 31/427
USPC ........................................................ 514/369
See application file for complete search history.

(56) References Cited

U.S. PATENT DOCUMENTS 6,887,877 B2    5/2005   Chan Chun Kong et al.
7,964,580 B2 *  6/2011   Sofia et al. ...................... 514/51

(Continued)

OTHER PUBLICATIONS

Talele et al. "Structure-based virtual screening, synthesis and SAR of novel inhibitors of hepatitis C NS5B polymerase," Bioorganic & Medicinal Chemistry, 2010, vol. 18, pp. 4630-4638.*

(Continued)

*Primary Examiner* — Shengjun Wang
(74) *Attorney, Agent, or Firm* — Haukaas Fortius PLLC; Michael H. Haukaas

(57) ABSTRACT

The invention provides methods to inhibit the replication of a flavivirus, methods of inhibiting the guanosine triphosphate (GTP)-binding and guanylyltransferase activity of a flavivirus RNA capping enzyme, and methods of treating a subject infected with a flavivirus. The methods can include contacting a flavivirus with an effective amount of a thioxothiazolidine compound described herein, or a derivative thereof, such as a compound of Formula (I).

21 Claims, 31 Drawing Sheets

(51) Int. Cl.
*A61K 9/48* (2006.01)
*A61K 31/427* (2006.01)

(56) References Cited

U.S. PATENT DOCUMENTS

| | | | |
|---|---|---|---|
| 8,168,193 | B2 | 5/2012 | Ng et al. |
| 8,343,937 | B2 | 1/2013 | Sommadossi et al. |
| 2004/0072788 | A1* | 4/2004 | Bhat et al. .................. 514/46 |
| 2012/0148534 | A1 | 6/2012 | Glenn et al. |
| 2013/0090339 | A1 | 4/2013 | Wang et al. |

OTHER PUBLICATIONS

Sing et al. "Arylalkylidene Rhodanine with bulky and hydrophobic functional group as selective HCV NS3 protease inhibiitor," Bioorganic & Medicinal Chemistry, Letters, 2001, vol. 11, pp. 91-94.*

Geiss et al., "Analysis of Flavivirus NS5 Methyltransferase Cap Binding," J. Mol. Biol. (2009) 385: 1643-1654.
Geiss et al., "Focus on flaviviruses: current and future drug targets," Future Med. Chem. (2009) 1 (2): 327-344.
Geiss et al., "A High-Throughput Screening Assay for the Identification of Flavivirus NS5 Capping Enzyme GTP-Binding Inhibitors: Implications for Antiviral Drug Development," J Biomol Screen (Jul. 25, 2011) DOI: 10.1177/1087057111412183 (http://jbx.sagepub.com/content/early/2011/07/23/1087057111412183), 11 pp.
Stahla-Beek et al "Identification of a Novel Antiviral Inhibitor of the Flavivirus Guanylyltransferase Enzyme," J. Virol. (Jun. 6, 2012) 86 (16): 8730-8739. DOI: 10.1128/JVI.00384-12 (http://jvi.asm.org/).
Henderson et al., "Analysis of RNA Binding by the Dengue Virus NS5 RNA Capping Enzyme," PLoS ONE (Oct. 12, 2011) 6 (10): e25795. DOI: 10.1371/journal.pone.0025795, 9 pp.
Issur et al., "The flavivirus NS5 protein is a true RNA guanylyltransferase that catalyzes a two-step reaction to form the RNA cap structure," RNA (Oct. 22, 2009) 15: 2340-2350. DOI: 10.1261/ma.1609709.

* cited by examiner $C_{19}H_{13}ClN_2O_4S_2$     BG100

$C_{20}H_{17}NO_4S_2$     BG101

$C_{13}H_{10}ClNO_2S_2$     BG114

$C_{16}H_{13}NO_4S_2$     BG115

$C_{19}H_{13}ClN_2O_4S_2$     BG119

C20H15ClN2O4S2   BG120

C20H15ClN2O4S2   BG121

C20H15ClN2O4S2   BG122

C19H13ClN2O4S2   BG123

$C_{19}H_{15}NO_3S_2$

BG130

$C_{19}H_{13}FN_2O_4S_2$

BG131

$C_{19}H_{13}FN_2O_4S_2$

BG132

$C_{13}H_9Cl_2NO_3S_2$

BG133

$C_{15}H_{14}ClNO_3S_2$

BG134

$C_{19}H_{14}ClNO_3S_2$  BG135

$C_{17}H_{20}N_2OS_2$  BG136

$C_{12}H_{11}NOS_2$  BG137

$C_{21}H_{17}NO_3S_2$  BG138

$C_{17}H_{12}N_2O_6S_2$  BG139

$C_{18}H_{14}N_2O_6S_2$  BG140

C$_{14}$H$_{13}$NO$_5$S$_2$

BG311

C$_{12}$H$_7$BrClNO$_4$S$_2$

BG222

C$_{12}$H$_7$Br$_2$NO$_4$S$_2$

BG223

C$_{12}$H$_7$BrFNO$_3$S$_2$

BG224

C$_{12}$H$_7$Cl$_2$NO$_4$S$_2$

BG225

BG227

BG228

BG229

BG230

$C_{20}H_{15}BrN_2O_4S_2$

BG291

$C_{17}H_{13}NO_4S_2$

BG292

$C_{13}H_{10}FNO_3S_2$

BG321

$C_{13}H_9Cl_2NO_3S_2$

BG324

$C_{12}H_9NO_3S_2$

BG325

$C_{21}H_{16}N_2O_6S_2$    BG352

$C_{19}H_{15}BrN_2O_3S_2$    BG353

$C_{19}H_{15}BrN_2O_3S_2$    BG354

$C_{19}H_{15}BrN_2O_3S_2$    BG355

$C_{20}H_{15}BrN_2O_4S_2$    BG356

Series 1b $C_{20}H_{15}BrFNO_6S$    BG163

$C_{21}H_{19}NO_5S$    BG166

$C_{16}H_{16}N_2O_2S$    BG172

$C_{22}H_{17}ClN_4O_5S_3$    BG174

C₁₆H₁₀ClNO₅S  BG175

C₁₃H₁₁NO₅S  BG215

C₁₂H₈ClNO₄S  BG226

Series 1c

| Structure | Compound |
|---|---|
|  $C_{17}H_{21}NO_3S_2$ | BG296 |

THIOXOTHIAZOLIDINE INHIBITORS

RELATED APPLICATIONS

This application claims priority under 35 U.S.C. §119(e) to U.S. Provisional Patent Application No. 61/653,559, filed May 31, 2012, which is incorporated herein by reference.

GOVERNMENT SUPPORT

This invention was made with government support under Grant No. AI065357 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 28, 2013, is named SequenceListing.txt and is 755 bytes in size.

BACKGROUND OF THE INVENTION

Arthropod-borne virus infections remain a major cause of morbidity and mortality worldwide. More than two billion people are at risk of infection with dengue virus (DEN) and 600 million people at risk of infection with yellow fever virus (YF) (20). Globally, an estimated 50-100 million cases of DEN and 200,000 cases of YF are reported each year, which infections result in approximately 20,000 (DEN) and 30,000 (YF) deaths annually (11). There are currently no clinically useable chemotherapeutic options for the treatment of any flavivirus infection, making it essential that new strategies and targets for the treatment of flavivirus infections be identified.

Flaviviruses are small enveloped, single-stranded positive sense RNA viruses with genomes consisting of approximately 11,000 kb RNA with a 5' type 1 RNA cap (23). The viral genome is translated as a single open reading frame (ORF) encoding a polyprotein precursor that is processed into three structural proteins (capsid, premembrane, and the envelope) and eight nonstructural proteins (NS1, NS2A, NS2B, NS3, NS4A, 2K, NS4B and NS5) by viral and cellular proteases (16). Currently, four viral enzymes are being studied as targets for antiviral drug discovery, including the NS3 helicase and protease enzymes and the NS5 RNA dependent RNA polymerase and capping enzymes (8).

In particular, the capping enzyme has received a good deal of attention as a novel antiviral drug target. The flavivirus capping enzyme has three distinct functions that can be targeted for therapeutic intervention: the N7/2'-O methyltransferase reactions (2, 3, 6, 9) and the recently discovered guanylyltransferase reaction (10, 13, 14). The formation of the 5' cap structure is critical to the survival of the virus for several reasons, including directing viral polyprotein translation and protecting the 5' end of the genome from cellular exonucleases. It has also been shown that a fully mature type 1 cap is a mechanism that cells use to discriminate self from non-self RNAs, and interference with the formation of a mature type 1 cap on the flavivirus genome limits viral replication (5, 28).

The flavivirus NS5 N-terminal capping enzyme is highly conserved across the flavivirus genus, and the guanosine triphosphate (GTP) and S-adenosyl methionine (SAM) binding sites, as well as the overall structure of the enzyme, are well conserved (4, 7, 9, 18, 27). The critical nature of the capping enzyme in viral replication and immune evasion, as well as its conservation across the flavivirus genus, position the capping enzyme as an important target for antiviral development efforts. The methyltransferase activity has been the primary capping enzyme target for drug development (15, 21), and ribavirin triphosphate has been observed to bind to and displace GTP from the enzyme (1). However, more effective inhibitors are needed to advance the clinical applications of these efforts.

While arthropod-borne flavivirus infection causes serious morbidity and mortality worldwide, there are currently no effective antiviral chemotherapeutics available for human use. Accordingly, new virus-specific targeting compositions and methods are urgently needed.

SUMMARY

The invention provides new compounds and methods for use as broadly active flavivirus therapeutics. The 2-thioxothiazolidin-4-ones have been identified as a family of compounds that provide potent biochemical inhibition of GTP binding and guanylyltransferase function of the capping enzyme. One 2-thioxothiazolidin-4-one, (E)-3-(5-(4-tert-butylbenzylidene)-4-oxo-2-thioxo-1,3-thiazolidin-3-yl)propanoic acid (BG-323), was found to possess significant antiviral activity in a dengue virus subgenomic replicon assay. Further testing of BG-323 demonstrated that this molecule is able to reduce the replication of infectious West Nile and yellow fever viruses with low toxicity. Disclosed herein are the first inhibitors that target the GTP-binding/guanylyltransferase activity of the flavivirus RNA capping enzyme. The invention thus provides compounds, compositions, and methods for inhibiting the flavivirus guanylyltransferase enzyme, and methods of treating conditions that benefit from inhibition of the flavivirus guanylyltransferase enzyme.

Accordingly, the invention provides compounds that inhibit the GTP binding and guanylation activity of flavivirus NS5 capping enzymes. The flavivirus capping enzyme is responsible for forming the 5' RNA cap on the viral genome, and possesses GTP binding and guanylyltransferase activity involved in forming the RNA cap. Lead compounds such as BG-323 possess biochemical activity against GTP binding by the dengue and yellow fever capping enzymes with a Ki of ~7 µM and a therapeutic index ($CC_{50}/EC_{50}$) against dengue replicon replication of 12. In silico docking of BG-323 provides the likely site of action as the GTP binding pocket/putative guanylyltransferase active site. Ribavirin, a known antiviral compound that has been previously shown to bind to the same site, has a therapeutic index of about 4 in the same assays, demonstrating that BG-323 has significantly improved activity. Based on knowledge of the CE binding site, BG-323 and analogs thereof can provide new antiviral therapeutics for treatment of mosquito-borne flavivirus infections.

The only chemical that is currently known to interfere with the flavivirus capping enzyme is ribavirin, a guanosine analog that has multiple modes of action against virus infection and is toxic to cells. BG-323 and analogs thereof have increased antiviral activity against dengue replication compared to ribavirin, therefore they can be more useful as an antiviral therapeutic against dengue and other flavivirus than ribavirin, and with reduced toxicity in various embodiments.

Accordingly, the invention provides methods for inhibiting the replication of a flavivirus comprising contacting the flavivirus with an effective inhibitory amount of a compound of Formula (I):

(I)

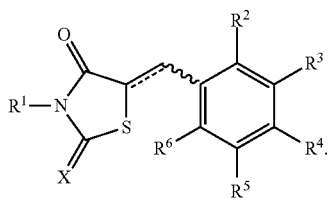

wherein

X is O or S;

$R^1$ is H, $-(CH_2)_nCO_2H$, $-(CH_2)_nC(=O)NHSO_2R^{10}$, $-(CH_2)_nC(=O)NH(aryl)$, $-(CH_2)_nC(=O)NH-(CH_2)_n$-(aryl), $-(CH_2)_nC(=O)NH$(heterocycle), $-(CH_2)_n$(heterocycle), $-(CH_2)_nC(=O)R^{11}$, alkyl, aryl, -aryl-amino, -aryl-alkoxy, $-(CHR^{10})_nCO_2H$, $-(CHR^{10})_nC(=O)NHSO_2R^{10}$, $-(CHR^{10})_nC(=O)N(R^{10})(R^{11})$, $-(CHR^{10})_nC(=O)NH-(CH_2)_n$-(aryl), $-(CHR^{10})_nC(=O)NH$(heterocycle), $-(CHR^{10})_nC(=O)NH$(heteroaryl), $-(CHR^{10})_n$(heterocycle), $-(CH_2R^{10})_nC(=O)R^{11}$, or $-(CH_2)_n$(aryl);

each n is independently 0, 1, 2, 3, or 4;

the dashed line represents an optionally present double bond;

the wavy bond represents E or Z olefin geometry when adjacent to a double bond;

$R^2$ is H, OH, alkyl, alkoxy, alkenyloxy, amino, nitro, halo, $-CF_3$, $-OSO_2$(aryl); or $-CO_2H$;

$R^3$ is H, OH, alkyl, alkoxy, alkenyloxy, aryloxy, benzyl, benzyloxy, amino, $-CF_3$, $-OSO_2$(aryl); $-CO_2H$, $-C(O)NH_2$, nitro, or halo;

$R^4$ is H, OH, alkyl, alkoxy, alkenyloxy, aryloxy, benzyl, benzyloxy, amino, $-CF_3$, $-OSO_2$(aryl); $-CO_2H$, $-C(O)NH_2$, nitro, or halo;

$R^5$ is H, OH, alkyl, alkoxy, alkenyloxy, aryloxy, benzyl, benzyloxy, amino, $-CF_3$, $-OSO_2$(aryl); $-CO_2H$, $-C(O)NH_2$, nitro, or halo;

$R^6$ is H, OH, alkyl, alkoxy, alkenyloxy, amino, nitro, halo, $-CF_3$, $-OSO_2$(aryl); or $-CO_2H$;

each $R^{10}$ is independently H, alkyl, aryl, benzyl, $-CF_3$, $-NH$(aryl), or $-NH$(heteroaryl);

each $R^{11}$ is independently H, OH, alkyl, $-CF_3$, alkoxy, aryl, aryloxy, benzyl, benzyloxy, amino, acyl ($-C(=O)R^{10}$), $-CO_2H$, $-C(O)NH_2$, nitro, or halo;

where any one of $R^2$-$R^6$ together with an adjacent phenyl carbon of Formula (I) optionally forms a 1,2-methylenedioxy group;

or a salt or solvate thereof;

wherein any alkyl, alkoxy, aryl, benzyl, benzyloxy, heterocycle, heteroaryl, or amino group can be optionally substituted with one or more (e.g., 1, 2, 3, 4, 5, or 6) $R^2$, $R^4$, $R^{10}$, or $R^{11}$ groups, 1,2-dioxymethylene groups, or 1,2-fuzed benzo groups.

When an aryl group is substituted with one of the various R groups (e.g., $R^2$, $R^3$, $R^4$, $R^{25}$, $R^6$, or $R^{10}$), the substitution can be ortho, meta, or para to the aryl group's connectivity to the rest of a molecule; for example, the R group can be located at the 2-, 3-, 4-, 5-, or 6-position of a phenyl ring.

In some embodiments, the hydrogen on the ylidine linking the thiazole and the phenyl groups of Formula (I) can be replaced with an alkyl group, such as a methyl, to form a tetrasubstituted olefin, as for BG-137. In other embodiments, a linking group can be inserted between the ylidine group of the thiazole ring and the phenyl group of Formula (I). Such linking groups can include an alkenylene group (e.g., ethylene) as for BG-138 and BG-326, or a heterocyclic diradical such a 2,5-furyl linking group, as for BG-139, BG-175, BG-177, BG-188, BG-279, BG-281, BG-282, BG-286, BG-290, and BG-292. In yet further embodiments, the phenyl ring of Formula (I) can be replaced by an imidazole group, optionally substituted with alkyl, as in BG-172. In some embodiments, the group $R^1$ must contain an H-bond donor or H-bond acceptor, such as an amine, an amide, an ether oxygen, a thio ether, a carbonyl, a hydroxyl, or a carboxylic acid.

The invention further provides methods of inhibiting the guanosine triphosphate (GTP)-binding and guanylyltransferase activity of a flavivirus RNA capping enzyme comprising contacting the RNA capping enzyme of a flavivirus with an effective inhibitory amount of a compound of Formula I as described above. Examples of specific compounds of Formula (I), and elements that can be used in any combination to provide other compounds of Formula (I), are shown in FIG. 6.

In some embodiments, the compound of Formula (I) can be a compound of Formula (II):

(II)

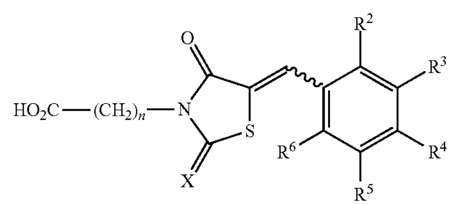

wherein n is 1, 2, or 3;

X is S or O;

$R^2$ is H, OH, alkyl, alkoxy, amino, nitro, halo, or carboxy;

$R^3$ is H, OH, alkyl, alkoxy, aryloxy, benzyl, benzyloxy, amino, nitro, halo, or carboxy;

$R^4$ is H, OH, alkyl, alkoxy, aryloxy, benzyl, benzyloxy, amino, nitro, halo, or carboxy;

$R^5$ is H, OH, alkyl, alkoxy, aryloxy, benzyl, benzyloxy, amino, nitro, halo, or carboxy;

$R^6$ is H, OH, alkyl, alkoxy, amino, nitro, halo, or carboxy;

or a salt or solvate thereof;

thereby inhibiting the replication of the flavivirus.

In various methods of the invention, the flavivirus can be the dengue virus, the yellow fever virus, the West Nile virus, including the NY99 strain of West Nile virus, and Powassan virus (a tick-borne flavivirus related to the BSL-4 level Tick-Borne Encephalitis virus).

In some specific embodiments, n is 1.

In other specific embodiments, n is 2.

In some specific embodiments, X is S.

In other specific embodiments, X is O.

In various embodiments, $R^2$ can be H, methoxy, hydroxy, or halo, and $R^6$ can be H.

In some embodiments, $R^4$ is H, phenoxy, benzyloxy, halo, or $(C_3$-$C_5)$alkyl.

In various embodiments, $R^3$ and $R^5$ are each independently H, halo, or methoxy.

In some embodiments, $R^4$ is not H. In other embodiments, at least one, at least two, at least three, at least four, or each, of $R^2$, $R^3$, $R^4$, $R^5$, and $R^6$ are not H.

In certain specific embodiments, the compound of Formula (II) is:

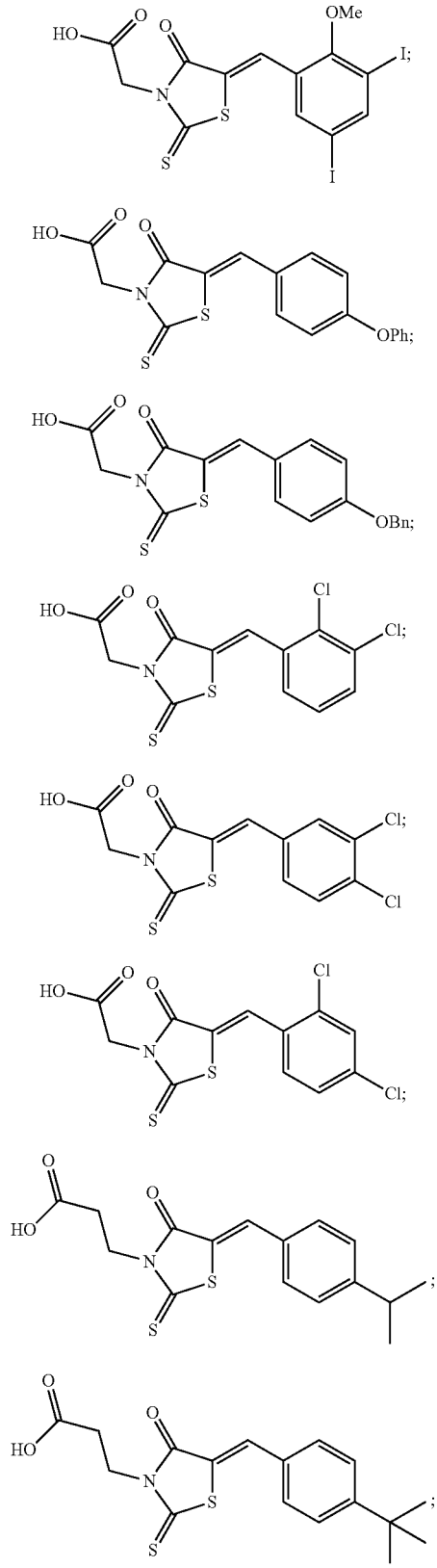

(BG-5); (BG-115); (BG-170); (BG-317); (BG-318); (BG-319); (BG-322); (BG-323);

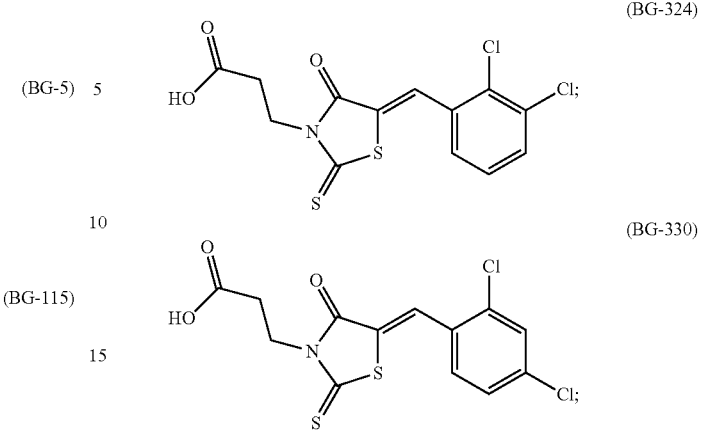

(BG-324); (BG-330);

or a salt or solvate thereof.

The invention further provides methods of inhibiting the guanosine triphosphate (GTP)-binding and guanylyltransferase activity of a flavivirus RNA capping enzyme comprising contacting the RNA capping enzyme of a flavivirus with an effective inhibitory amount of a compound of Formula II, thereby inhibiting the guanosine triphosphate (GTP)-binding and guanylyltransferase activity of the flavivirus RNA capping enzyme.

The flavivirus RNA capping enzyme can be an NS5 capping enzyme. The flavivirus RNA capping enzyme can be, for example, the dengue virus NS5 RNA capping enzyme. The compound of Formula (II) has a dengue virus Ki of less than about 45 µM, less than about 40 µM, less than about 30 µM, less than about 25 µM, less than about 20 µM, less than about 15 µM, or less than about 10 µM. The compound of Formula (II) has a yellow fever virus Ki of less than about 45 µM, less than about 40 µM, less than about 30 µM, less than about 25 µM, less than about 20 µM, less than about 15 µM, or less than about 10 µM.

The invention thus provides for the use of compounds of the formulas described herein for the manufacture of medicaments useful for the treatment of viral infections in a mammal, such as a human. The invention also provides for the use of the compositions described herein for use in medical therapy, such as treating viral infections, for example, in a mammal. Accordingly, the invention provides methods to treat a flaviviral infection in a subject in need thereof comprising administering to the subject a therapeutically effective amount of a compound of Formula (I). Medicaments and compositions comprising compounds of Formula (I) can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

Figure 1:
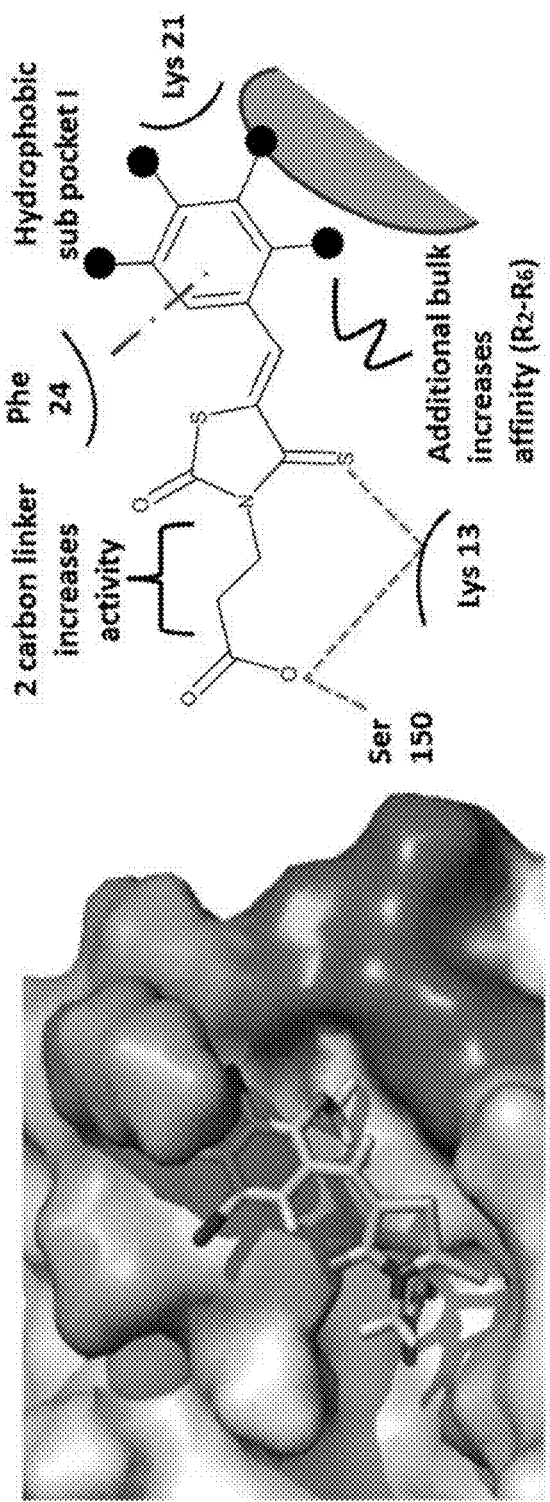
FIG. 1. SAR of Thioxothiazolidine binding. A) 3D rendering (left side of figure) of the predicted orientation of BG-5 within the yellow fever capping enzyme, as positioned in hydrophobic sub-pocket 1 ; and hydrophobic sub-pocket 2. BG-5 is depicted in stick form. B) Summary pharmacophore model (right side of figure) based on $K_i$ values for the dengue and yellow fever virus capping enzymes in Table 2. The dash and dotted line represents π/π stacking and the dashed lines represent predicted hydrogen bonds.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

Specific values listed below for radicals, substituents, and ranges, are for illustration only; they do not exclude other defined values or other values within defined ranges for the radicals and substituents. However, certain values or ranges of values can optionally be excluded from certain embodiments in the form of negative limitations.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent as described for Formula (I) or Formula (II), or a substituent as described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

Substituted alkyl groups include haloalkyl groups. The term "haloalkyl" refers to alkyl as defined herein substituted by 1-4 halo groups, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, perfluorooctyl, and the like.

The term "alkoxy" refers to the group -O-alkyl, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent (e.g., linking two groups together), and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine.

By way of example and not limitation, carbon bonded heterocycles can be bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like. Various combinations of the aforementioned positions are included in the compounds described herein.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, tetramethylene, or 1,2-methylenedixoy diradical thereto.

When an R group is an aryl, heteroaryl, or heterocycle, the group may be attached through use of a linking group or linker. Examples of linkers include alkylene groups. For example, a recited heterocycle substituent can be adjusted to include a linker, such as —$CH_2$-pipperidine or —$CH_2$—$CH_2$-pyrrolidine.

The term "halo" refers to fluoro, chloro, bromo, or iodo.

"Amino" refers to —$NH_2$. Amino groups can be substituted, for example with an alkyl group to form an "alkylamino", e.g., —$NR_2$, wherein at least one R is alkyl and the second R is alkyl or hydrogen. The term "acylamino" refers to RC(=O)NH—, wherein R is alkyl or aryl. The alkyl group can be, for example, a $C_1$-$C_6$ alkyl group. Examples include, but are not limited to, methylamino and ethylamino. The group may be a terminal group or a bridging group, and the alkyl groups may be substituted.

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replace by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure, and combinations thereof. Additionally, suitable substituent groups can be, e.g., —X, —R, —O⁻, —OR, —SR, —S⁻, —$NR_2$, —$NR_3$, =NR, —$CX_3$, —CN, —OCN, —SCN, —N=C=O, —NCS, —NO, —$NO_2$, =$N_2$, —$N_3$, —NC(=O)R, —C(=O)R, —C(=O)NRR, —S(=O)$_2$O⁻, —S(=O)$_2$OH, —S(=O)$_2$R, —OS(=O)$_2$OR, —S(=O)$_2$NR, —S(=O)R, —OP(=O) (OR)$_2$, —P(=O)(OR)$_2$, —OP(=O)(OH)(OR), —P(=O)(OH)(OR), —P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above can be excluded from the group of potential values for substituents on the substituted group. The various R groups in the schemes and figures of this disclosure can be one or more of the substituents recited above, thus the listing of certain variables for such R groups (including $R^1$, $R^2$, $R^3$, etc.) are representative and not exhaustive, and can be supplemented with one or more of the substituents above.

Alkyl chains of Formula (I) and Formula (II) can be optionally interrupted, for example, with one or more heteroatoms. The term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted", provided that each of the indicated atom's normal valency is not exceeded, and that the interruption results in a stable compound. Suitable groups that can interrupt a carbon chain include, e.g., with one or more non-peroxide oxy (—O—), thio (—S—), imino (—N(H)—), methylenedioxy (—$OCH_2O$—), carbonyl (—C(=O)—), carboxy (—C(=O)O—), carbonyldioxy (—OC(=O)O—), carboxylato (—OC(=O)—), imine (C=NH), sulfinyl (SO) and sulfonyl ($SO_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached. An alkyl group that is interrupted by a heteroatom therefor forms a heteroalkyl group.

Compounds of Formulas (I) and (II) can have recursive substituents. Selected substituents of compounds defined by the formulas described herein may be present to a recursive degree. In this context, "recursive substituent" means that a substituent may recite another instance of itself. Because of the recursive nature of such substituents, theoretically, a large number may be present in any given claim. Typically, a recursive substituent is present only one, two, three, or four times in one compound of a given formula. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. Recursive substituents can be present such that the molecular weight of compounds of a given formula is less than about 900, less than about 800, less than about 750, less than about 700, less than about 650, less than about 600, less than about 550, or less than about 500.

Recursive substituents are an intended aspect of the invention. One of ordinary skill in the art of medicinal and organic chemistry understands the versatility of such substituents. To the degree that recursive substituents are present in an embodiment, the total number will be determined as set forth above.

Figure 6:
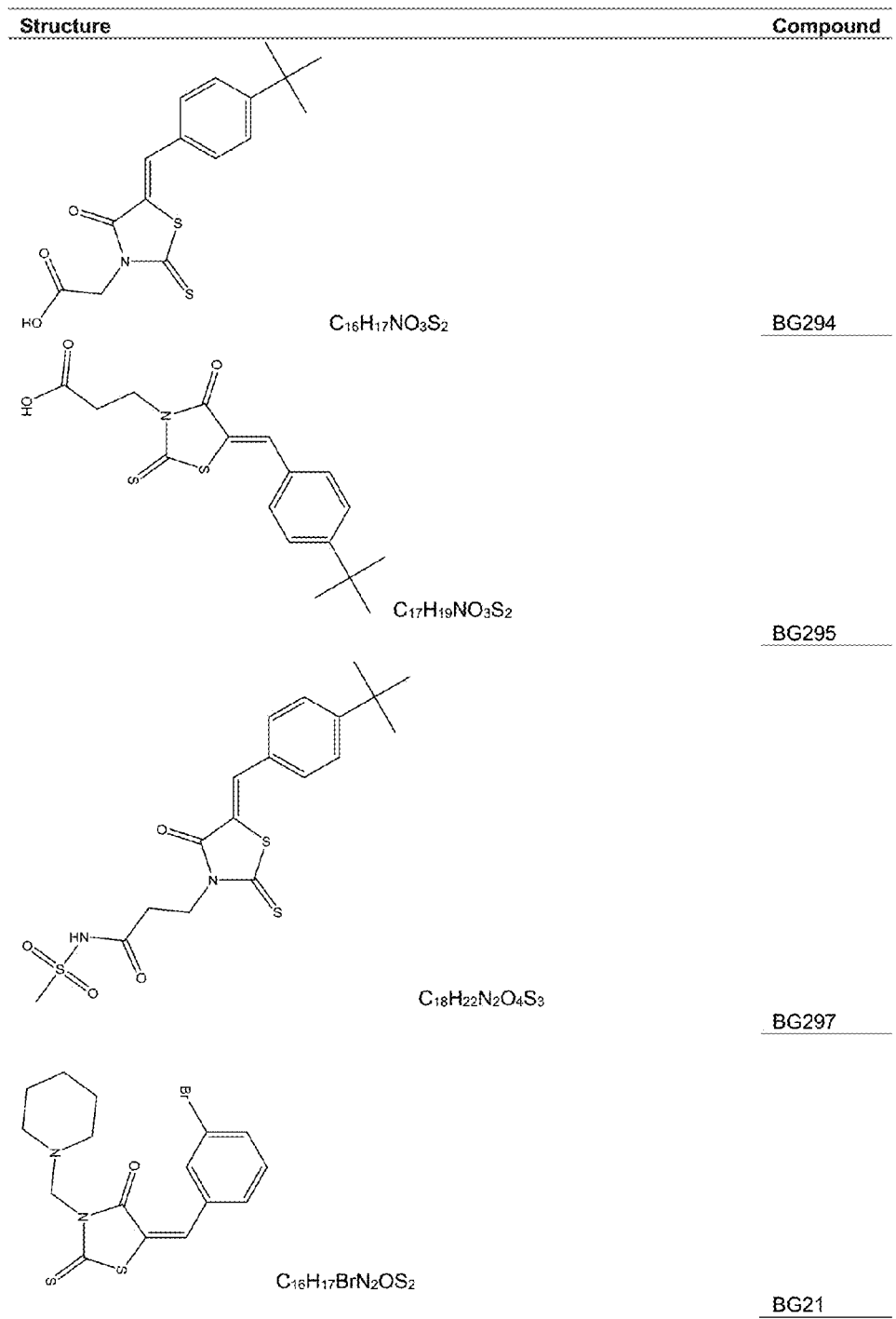
Figure 6:
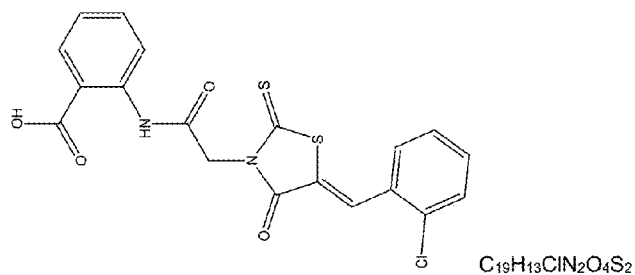
Figure 6:
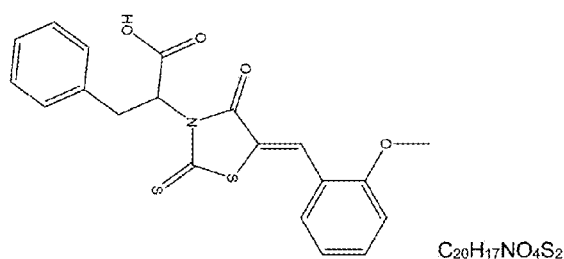
Figure 6:
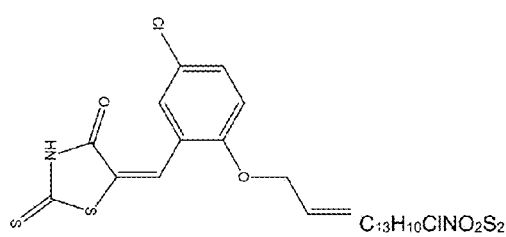
Figure 6:
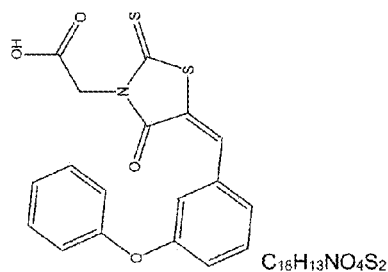
Figure 6:
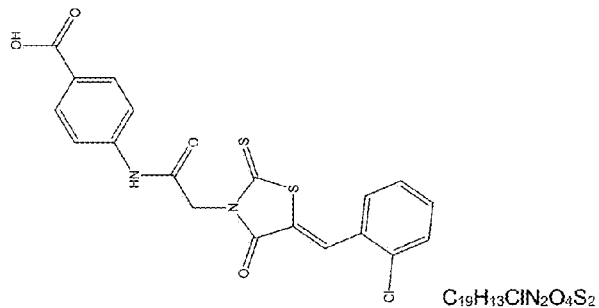
Figure 6:
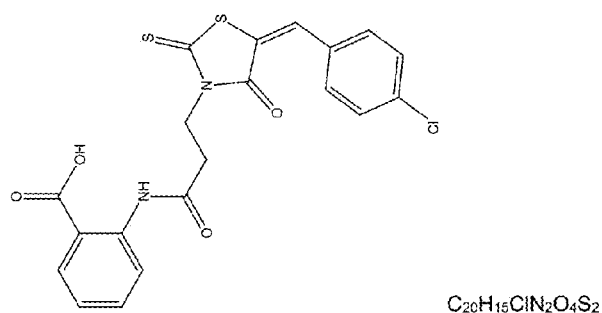
Figure 6:
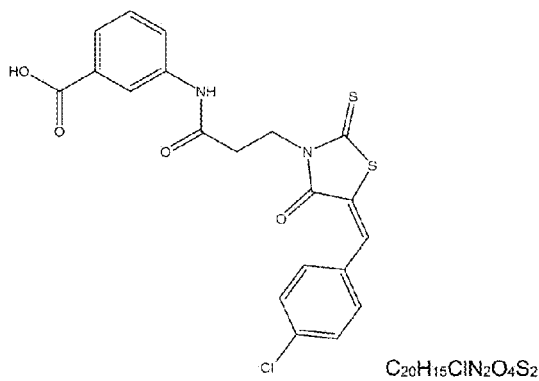
Figure 6:
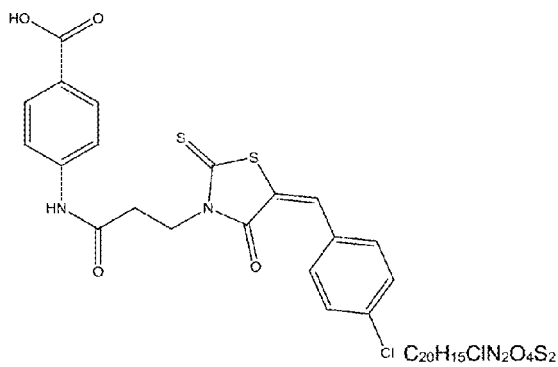
Figure 6:
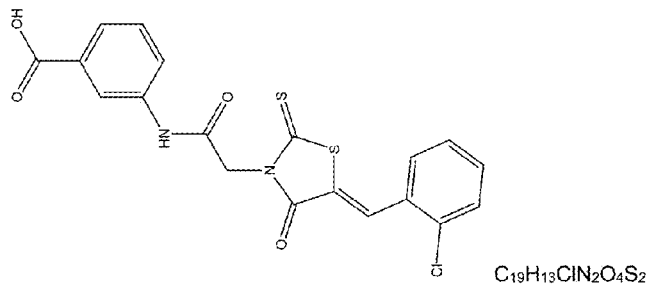
Figure 6:
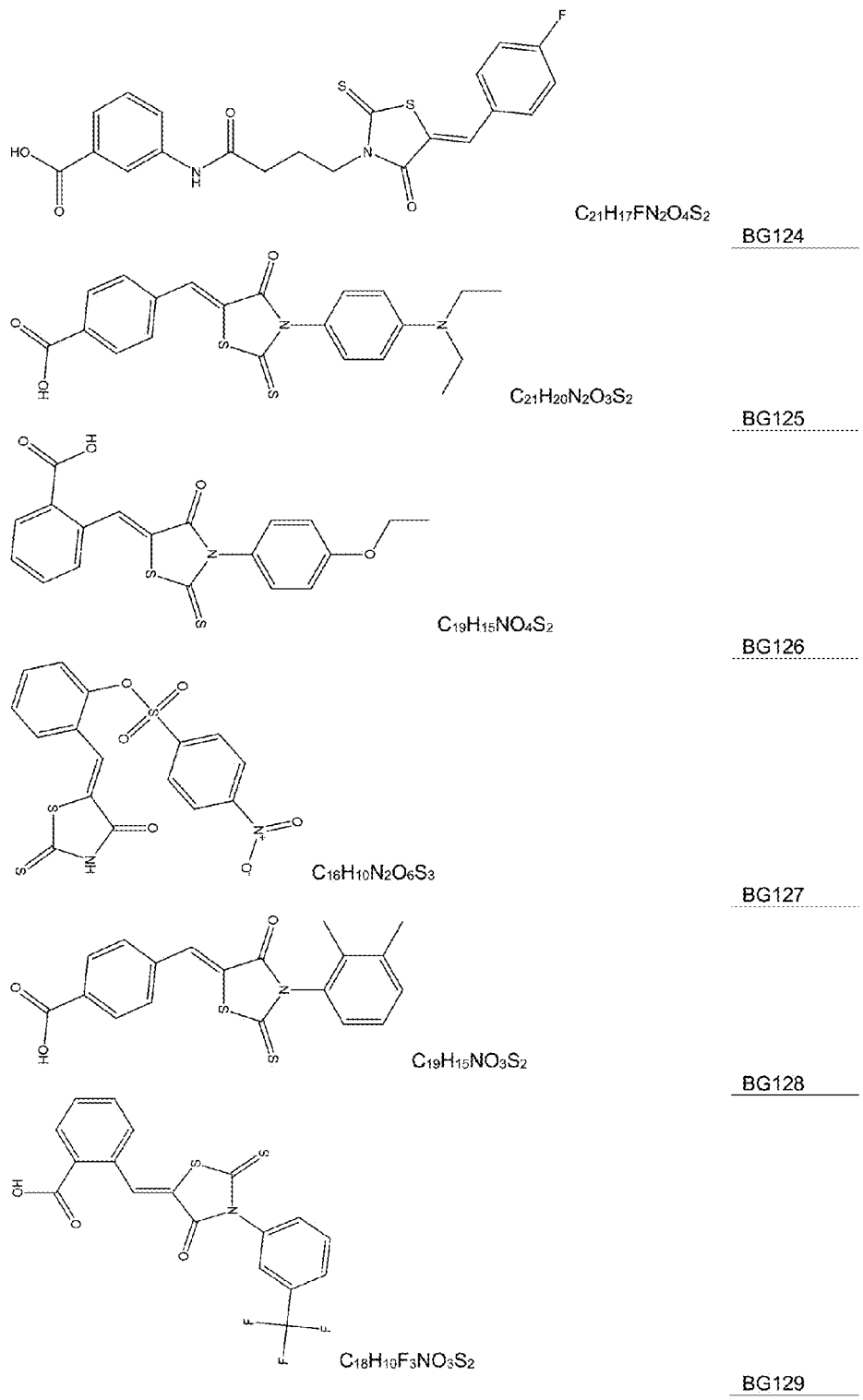
Figure 6:
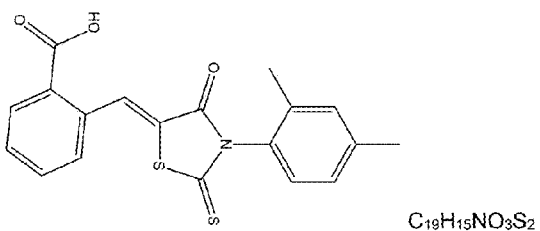
Figure 6:
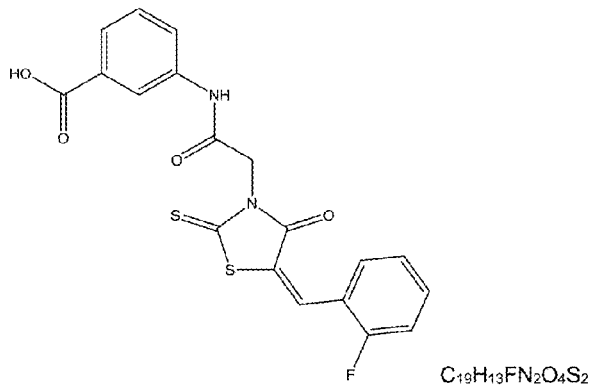
Figure 6:
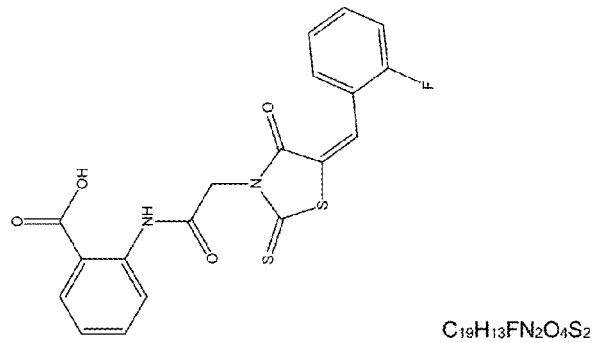
Figure 6:
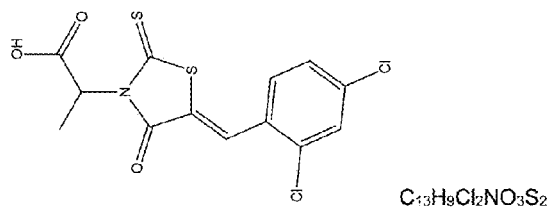
Figure 6:
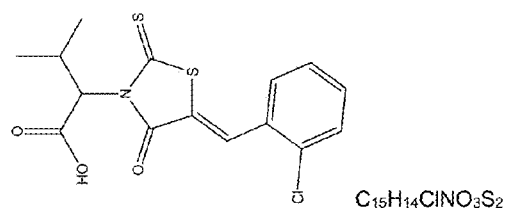
Figure 6:
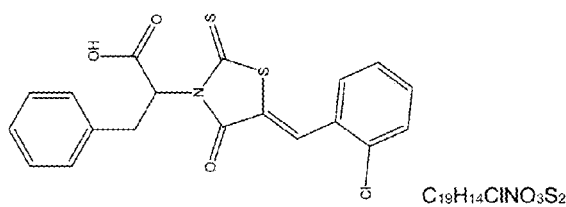
Figure 6:
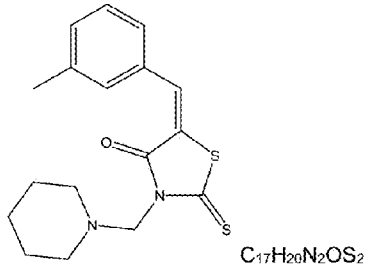
Figure 6:
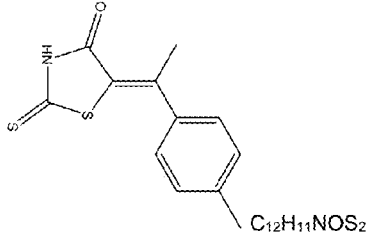
Figure 6:
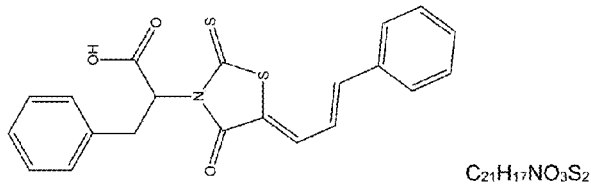
Figure 6:
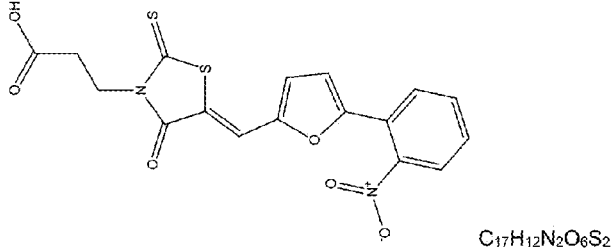
Figure 6:
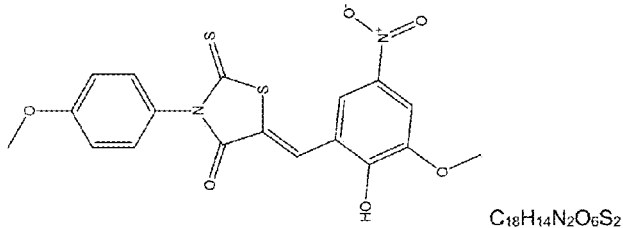
Figure 6:
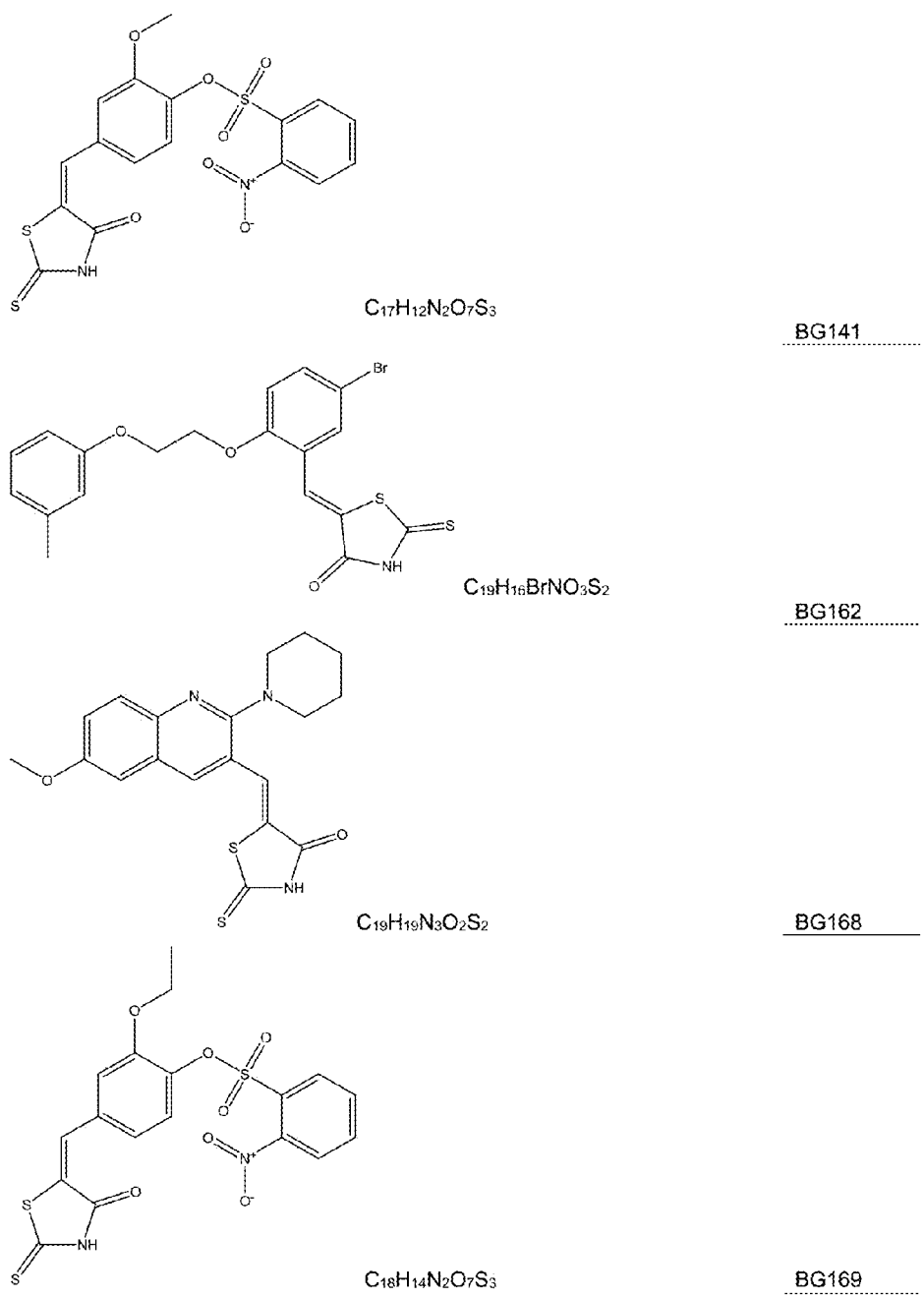
Figure 6:
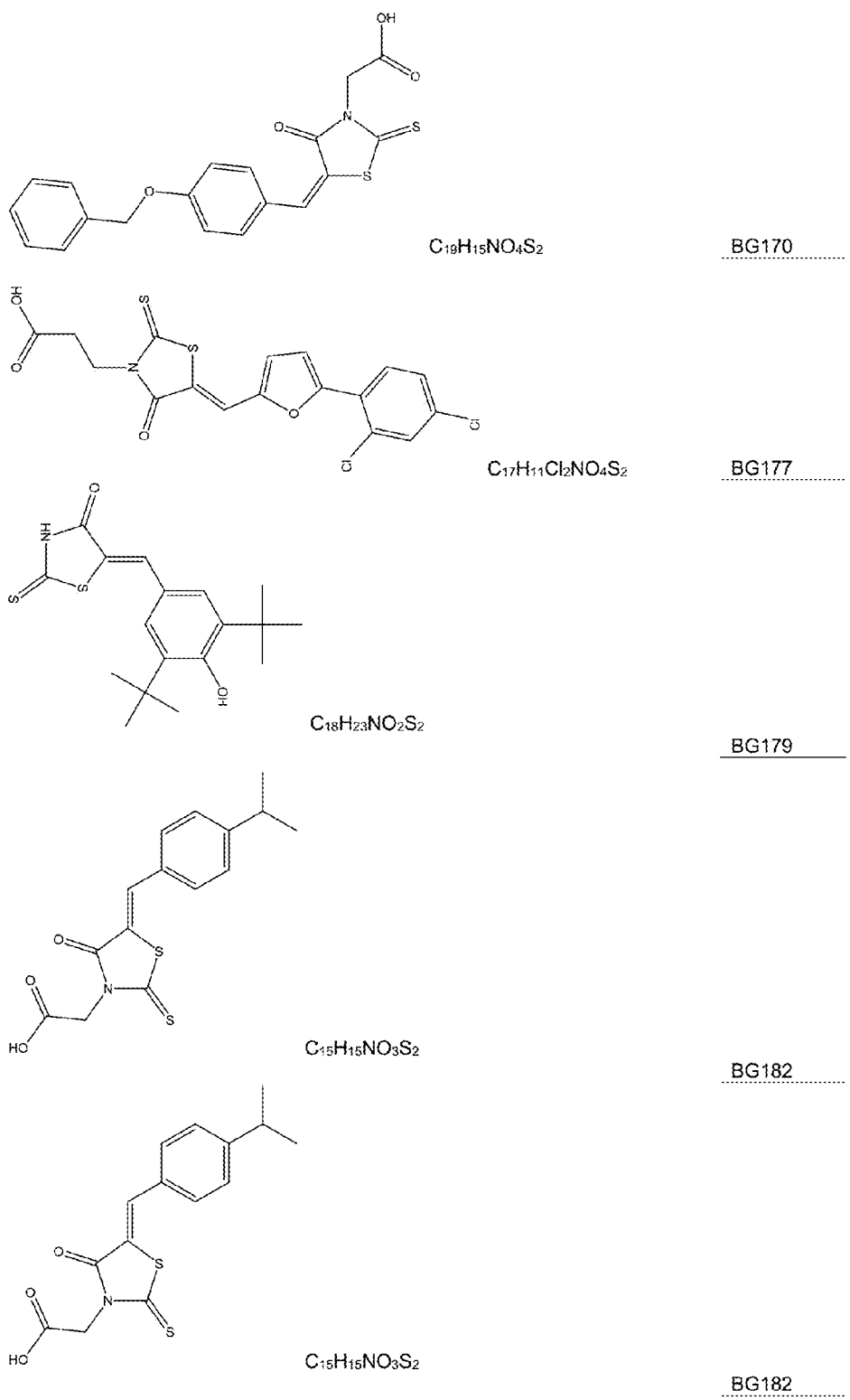
Figure 6:
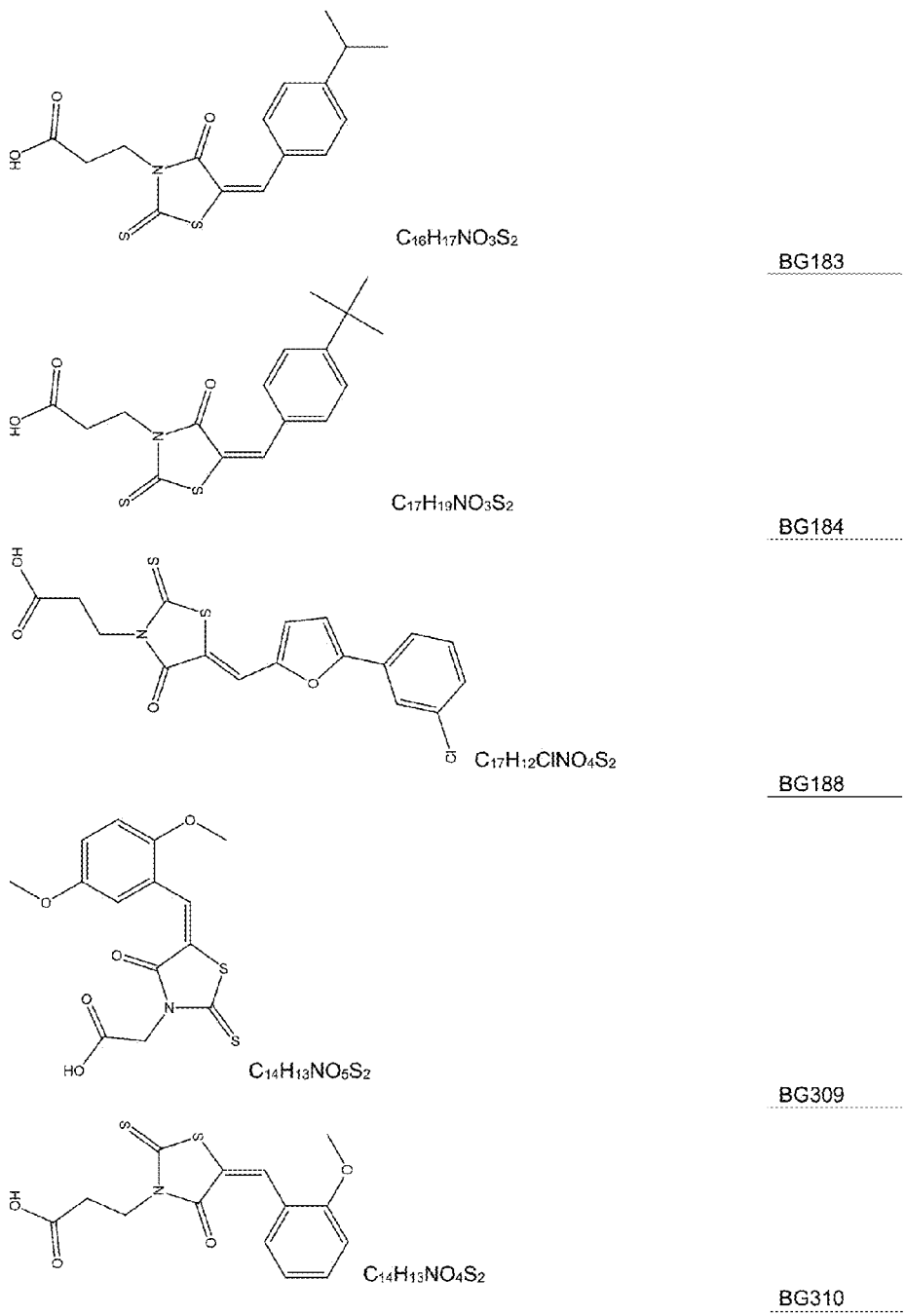
Figure 6:
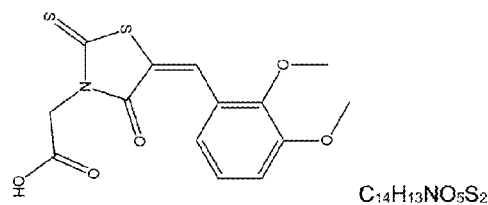
Figure 6:
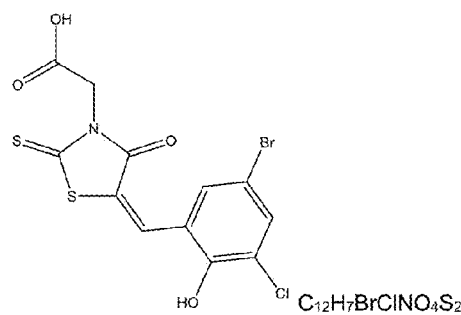
Figure 6:
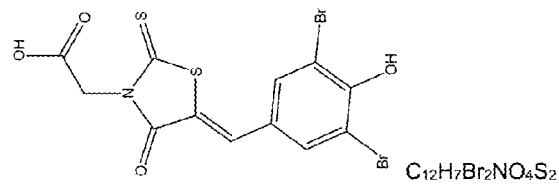
Figure 6:
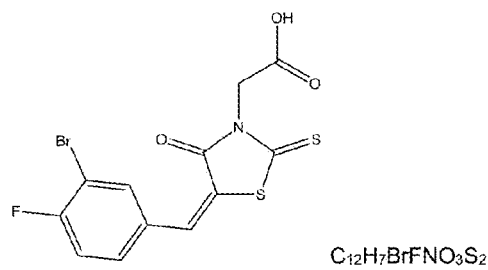
Figure 6:
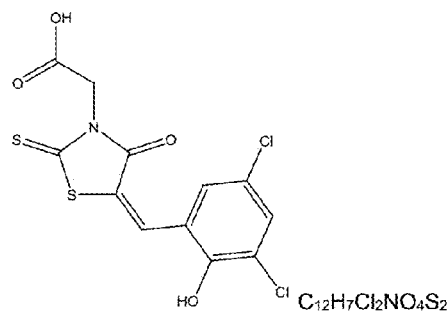
Figure 6:
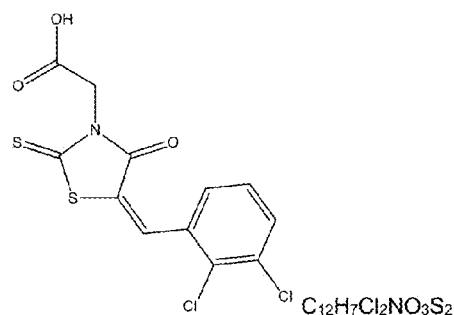
Figure 6:
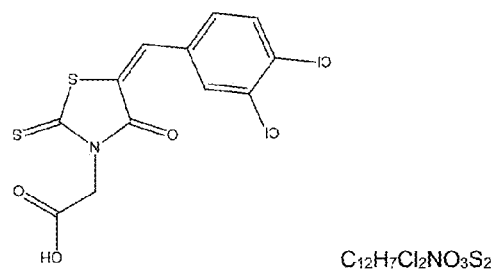
Figure 6:
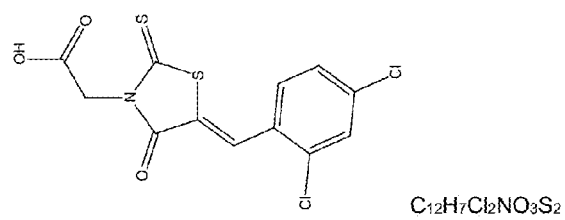
Figure 6:
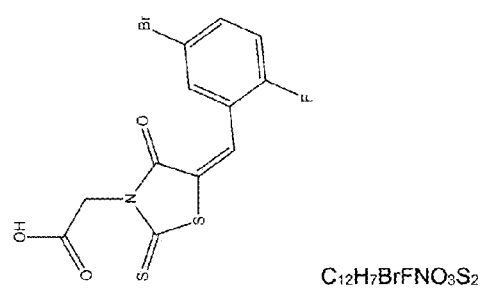
Figure 6:
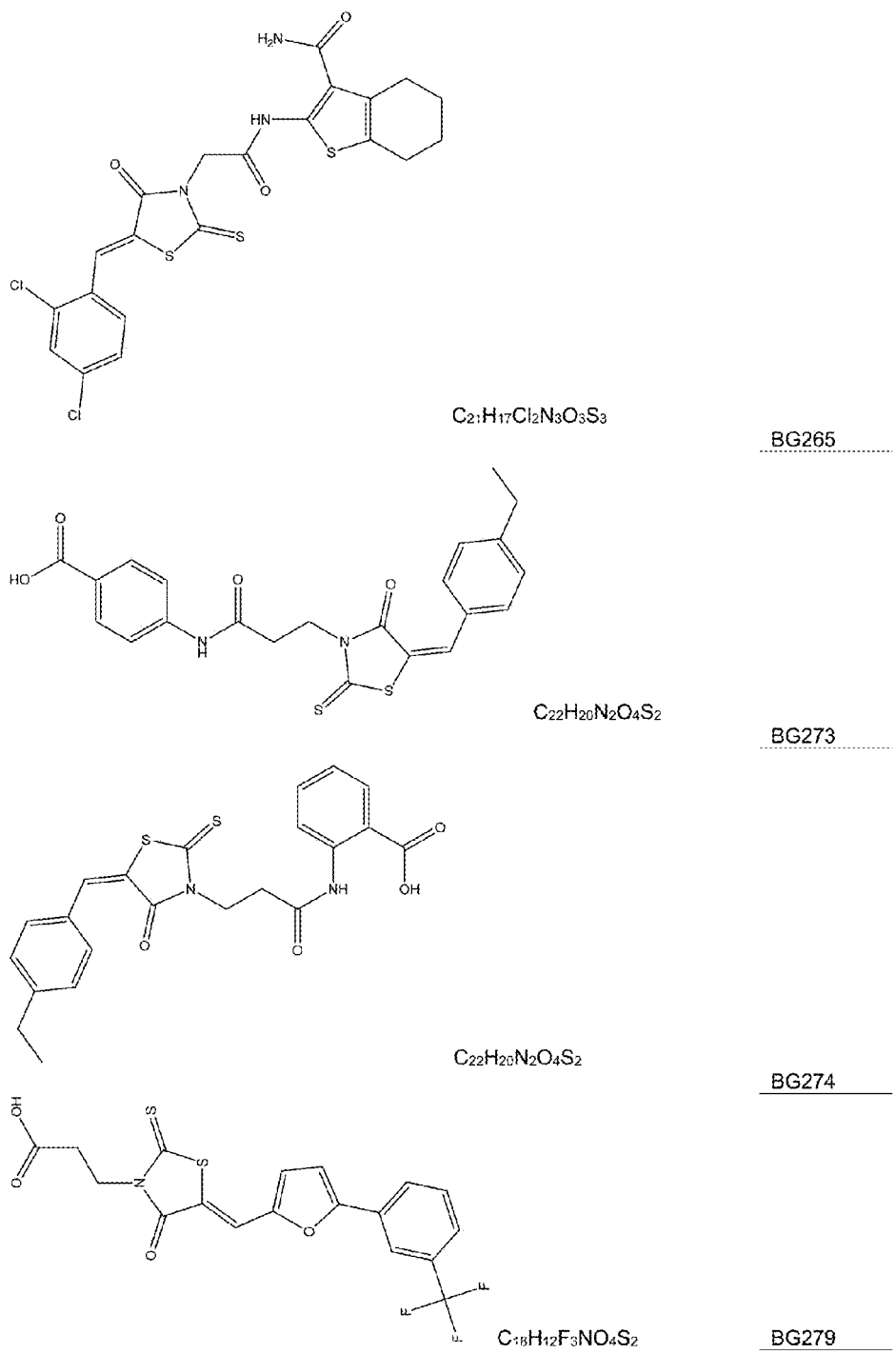
Figure 6:
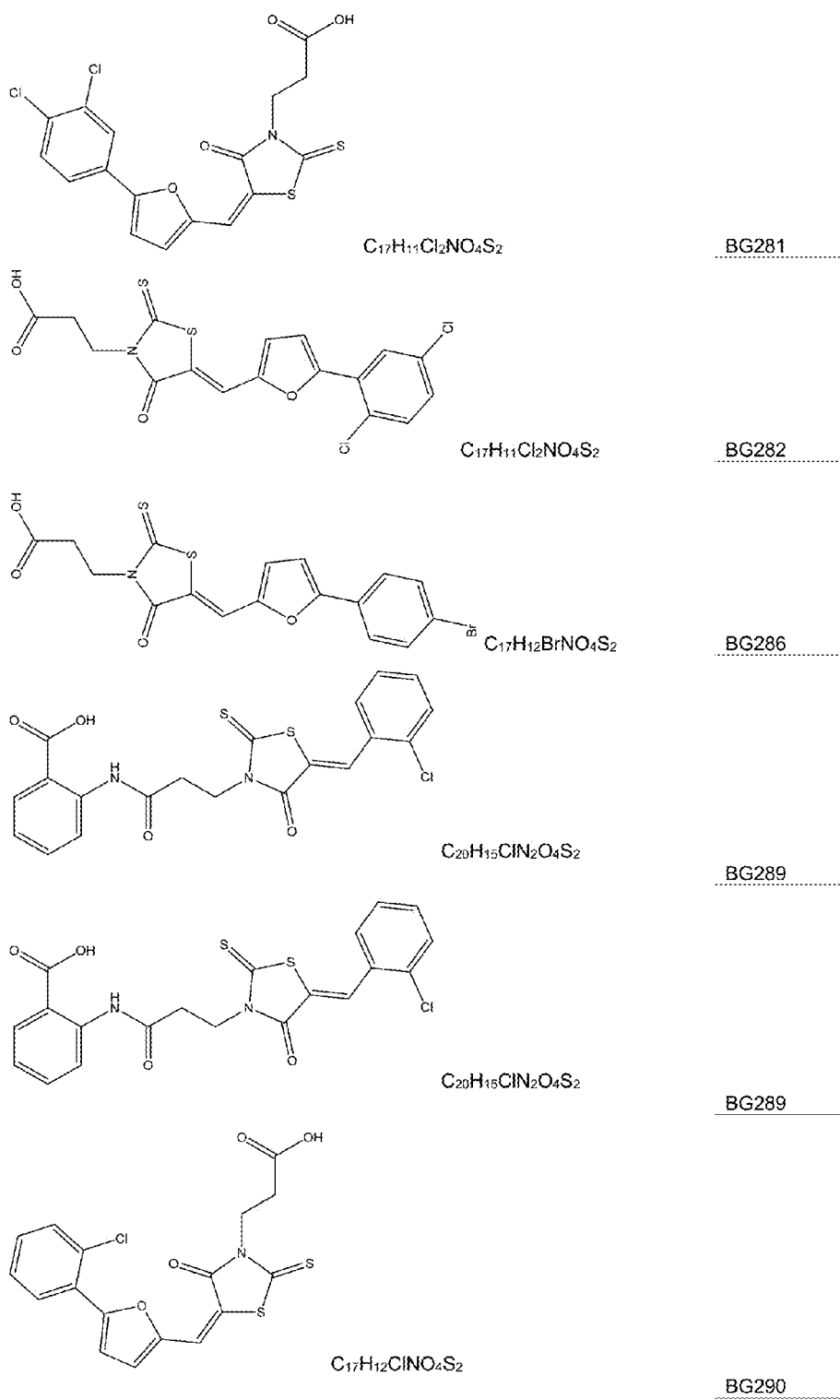
Figure 6:
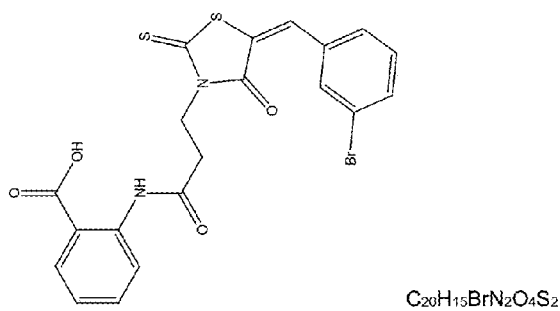
Figure 6:
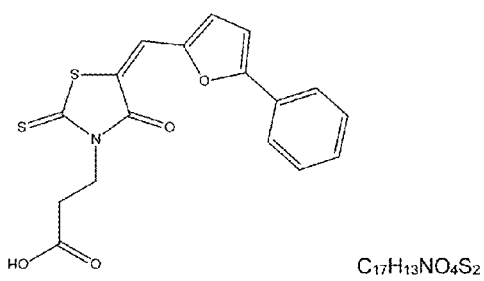
Figure 6:
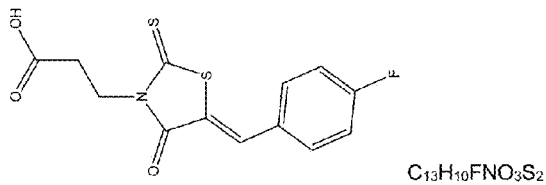
Figure 6:
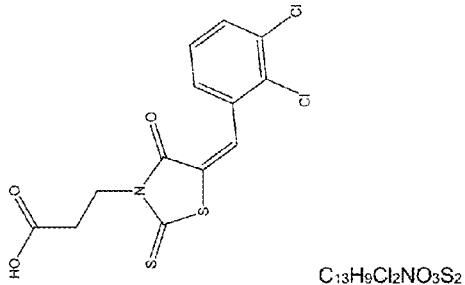
Figure 6:
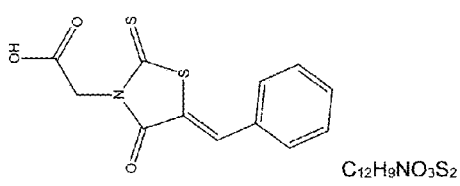
Figure 6:
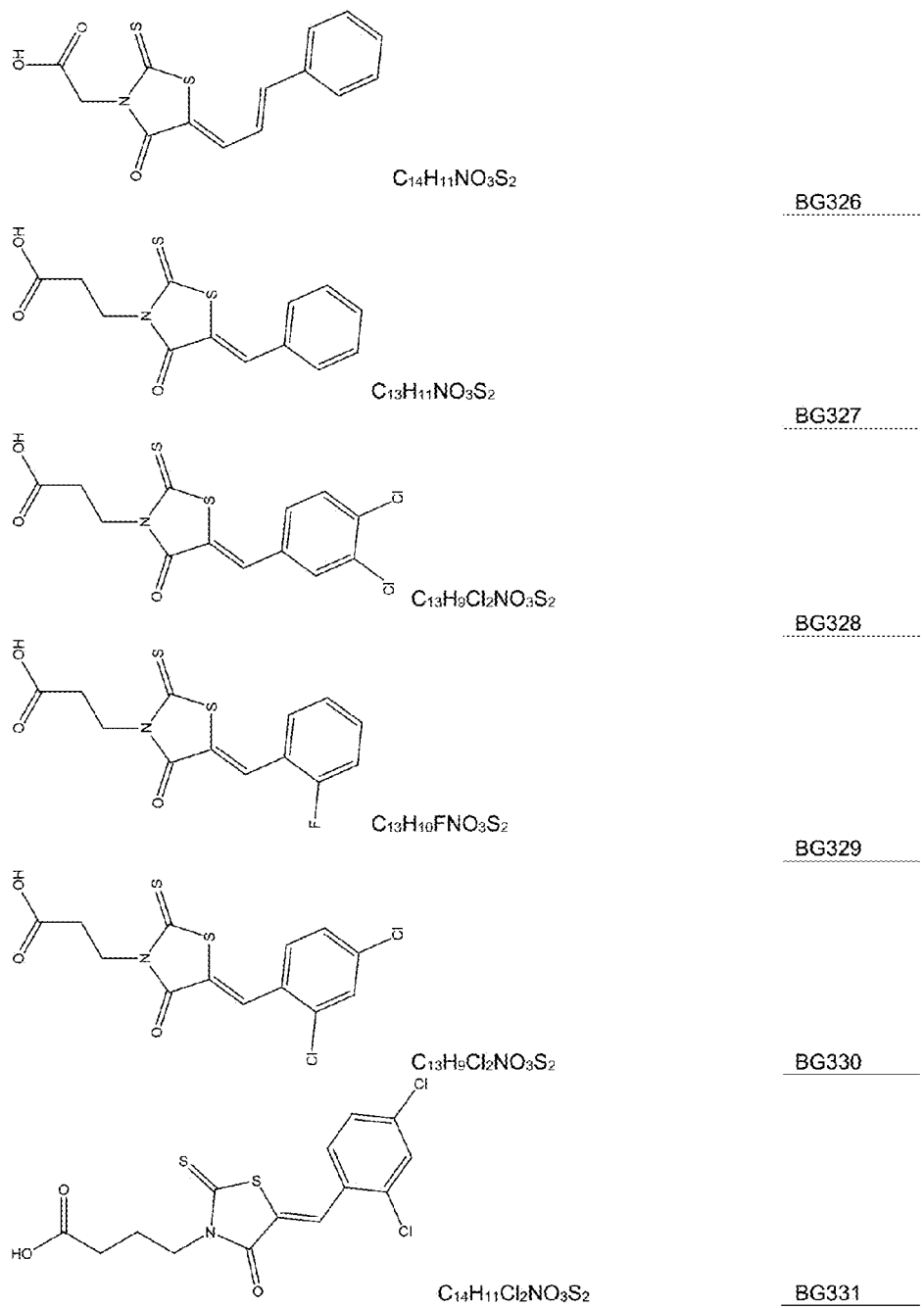
Figure 6:
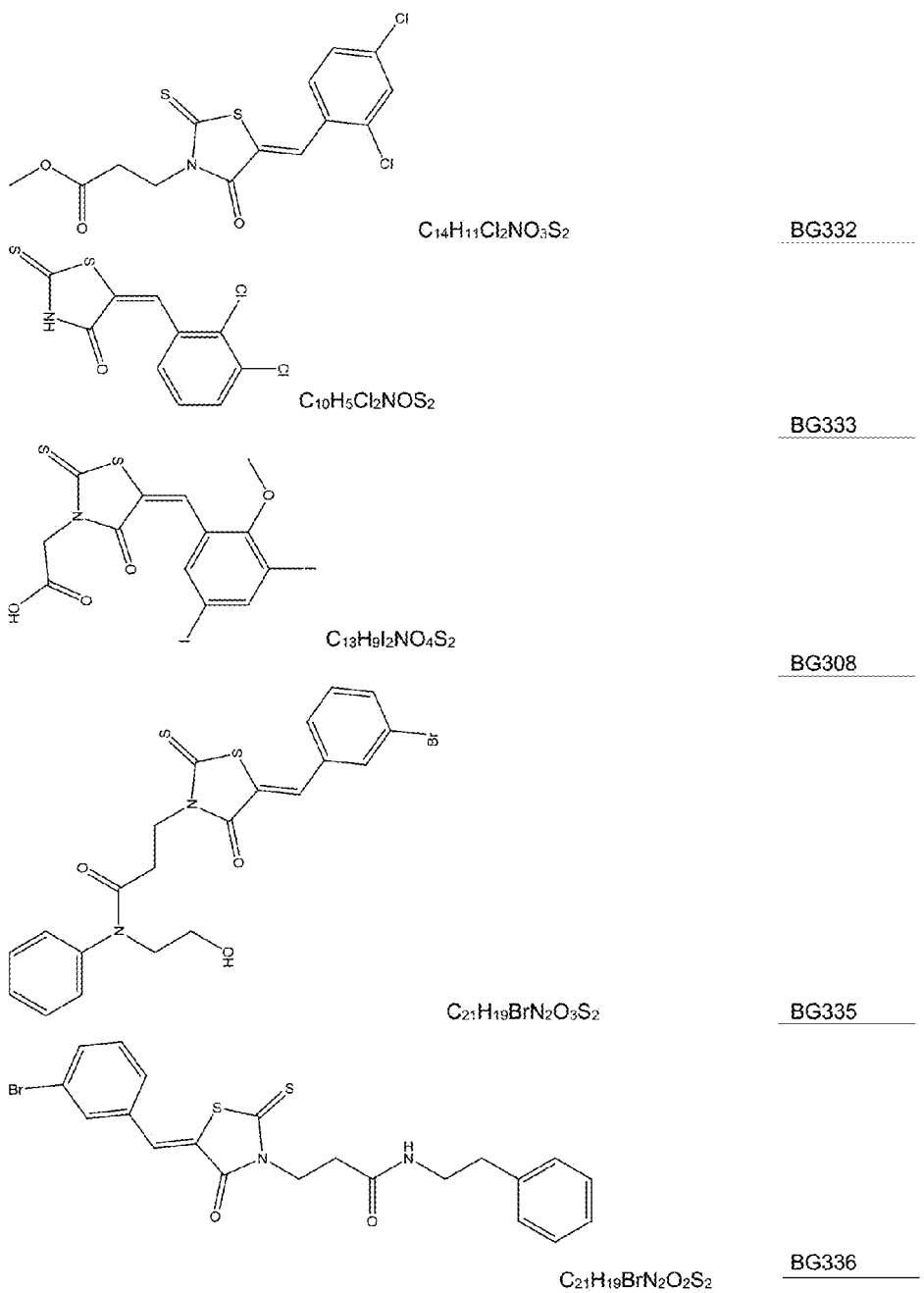
Figure 6:
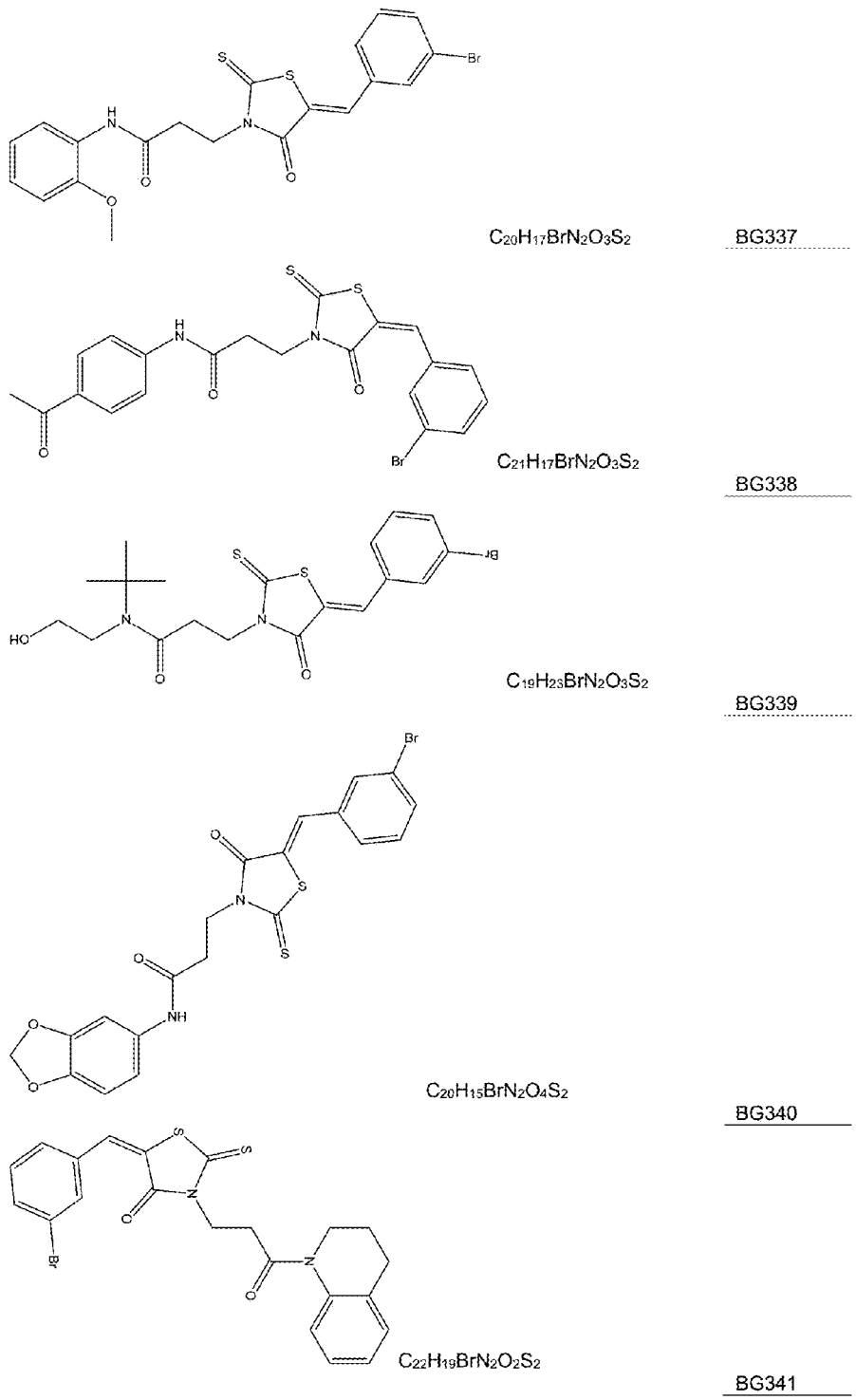
Figure 6:
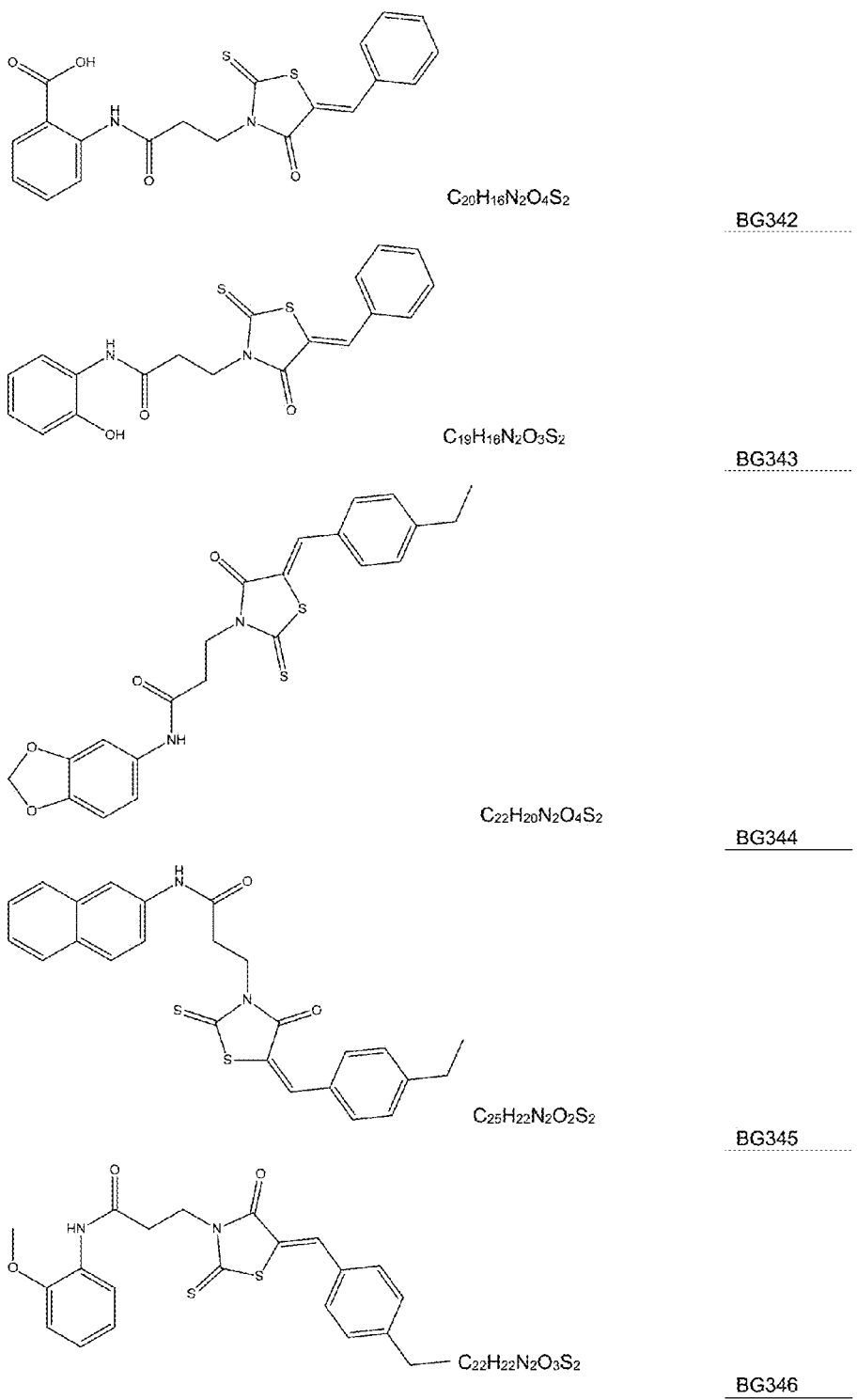
Figure 6:
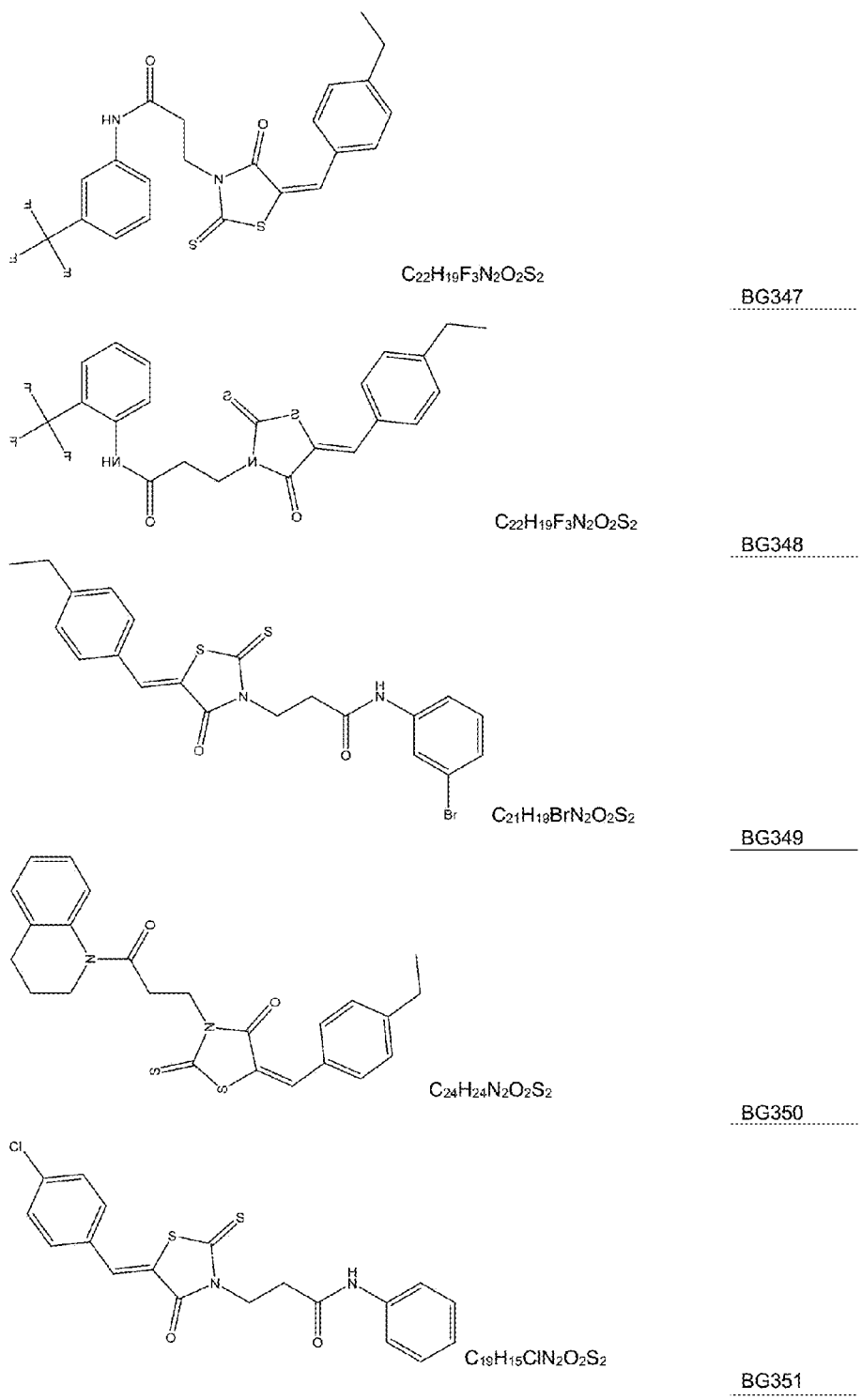
Figure 6:
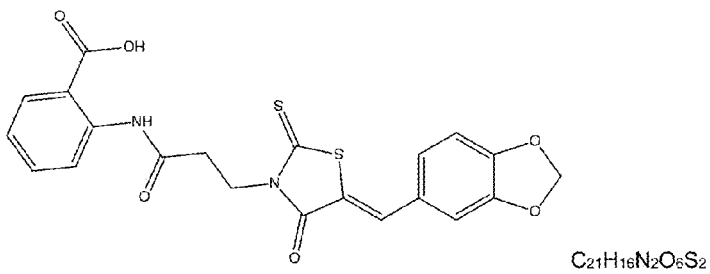
Figure 6:
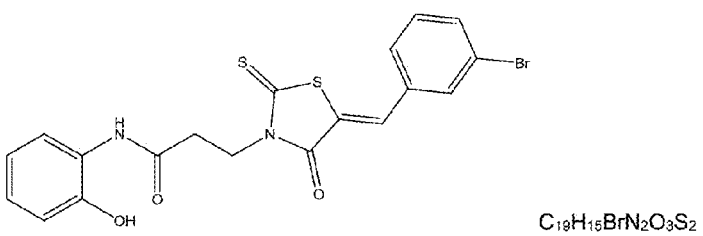
Figure 6:
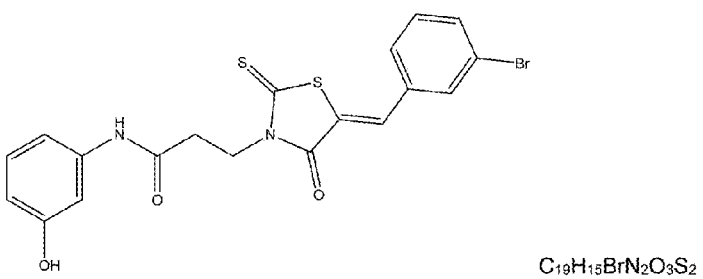
Figure 6:
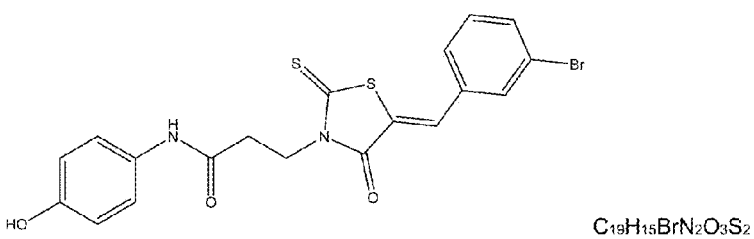
Figure 6:
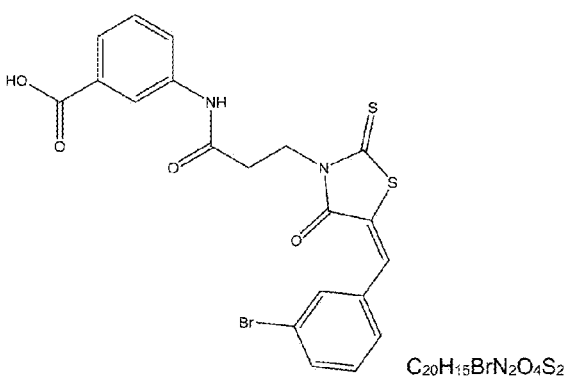
Figure 6:
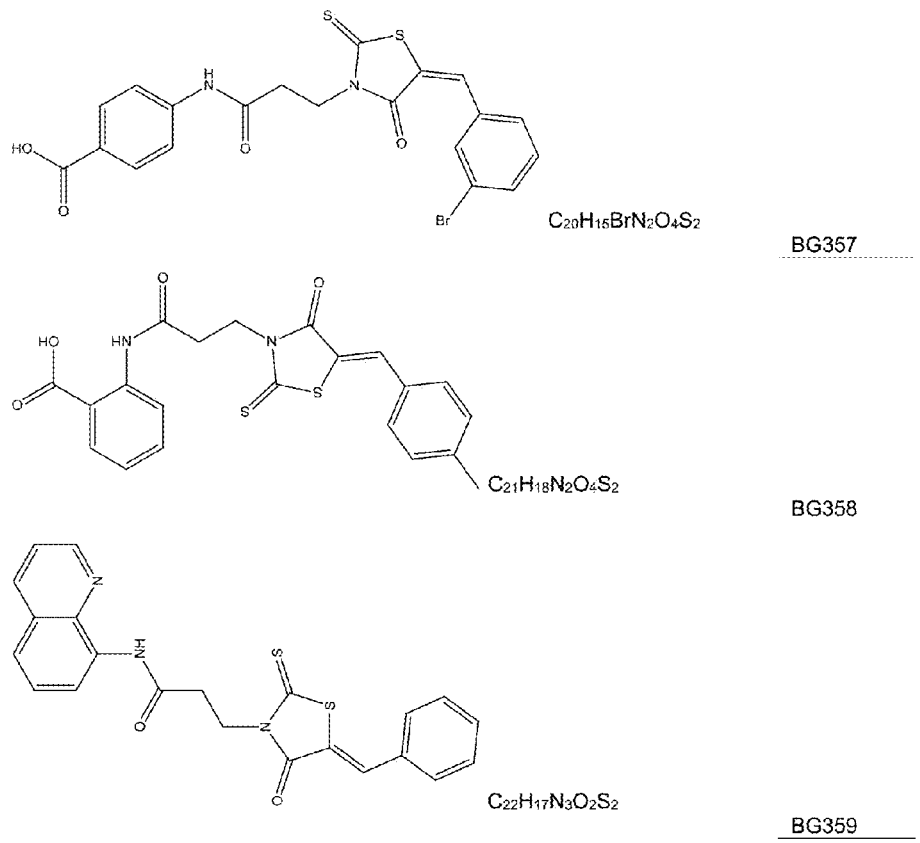
Figure 6:
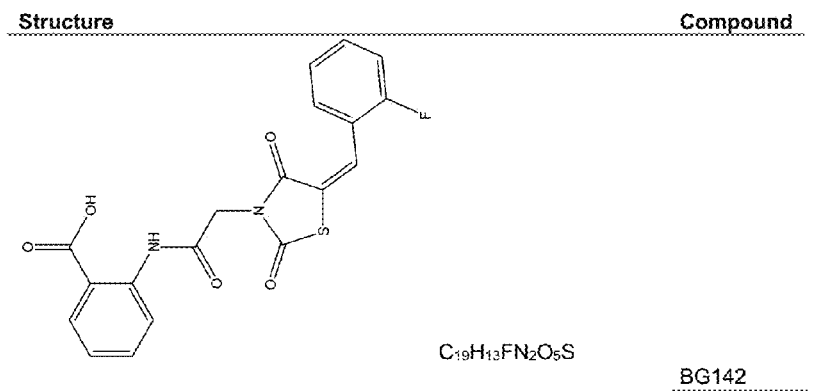
Figure 6:
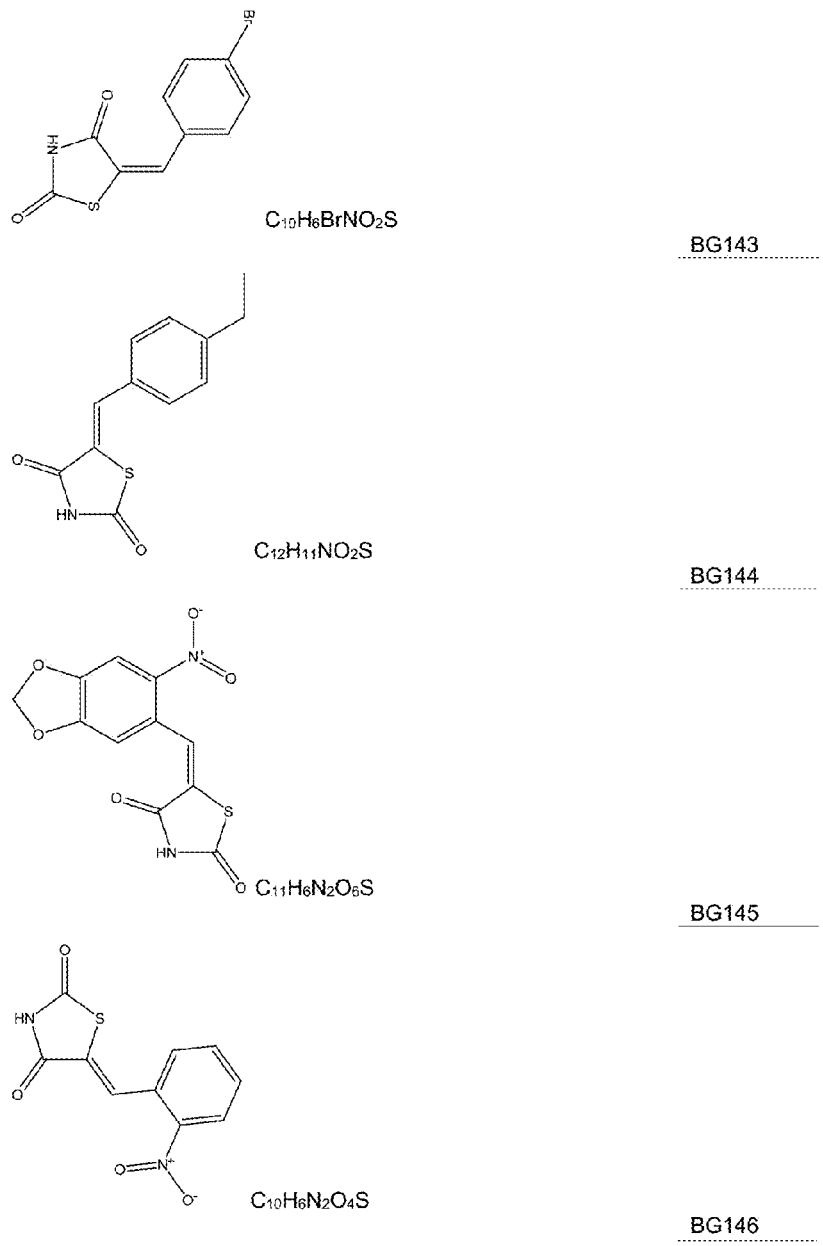
Figure 6:
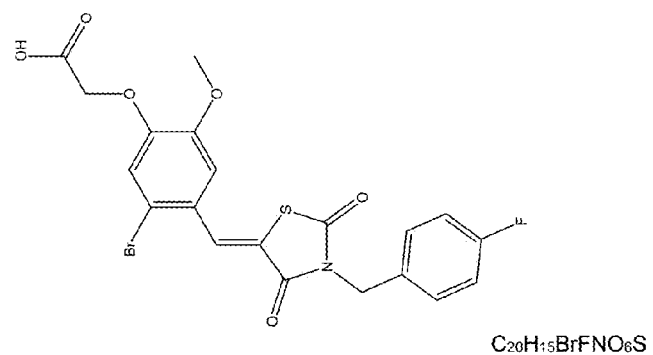
Figure 6:
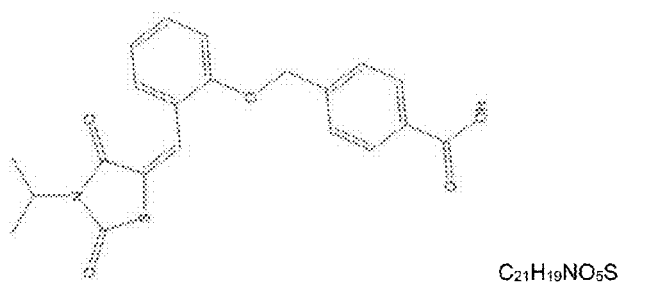
Figure 6:
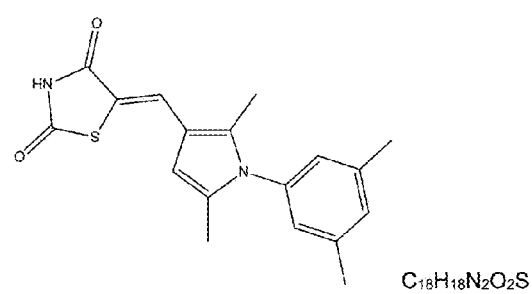
Figure 6:
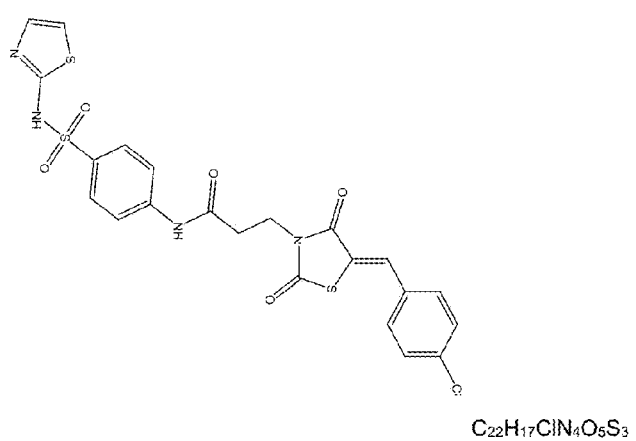
Figure 6:
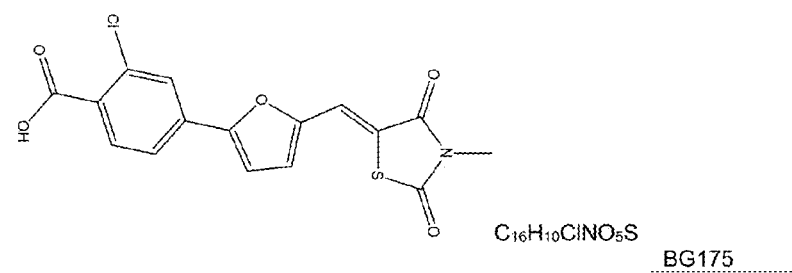
Figure 6:
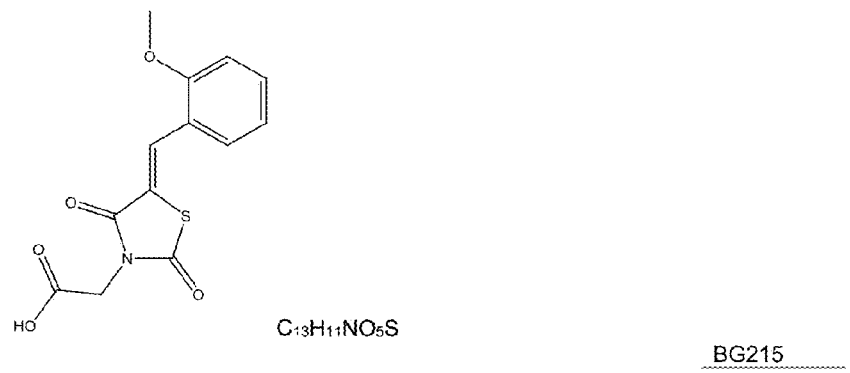
Figure 6:
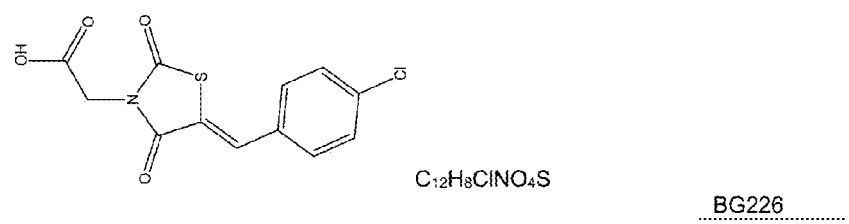
Figure 6:
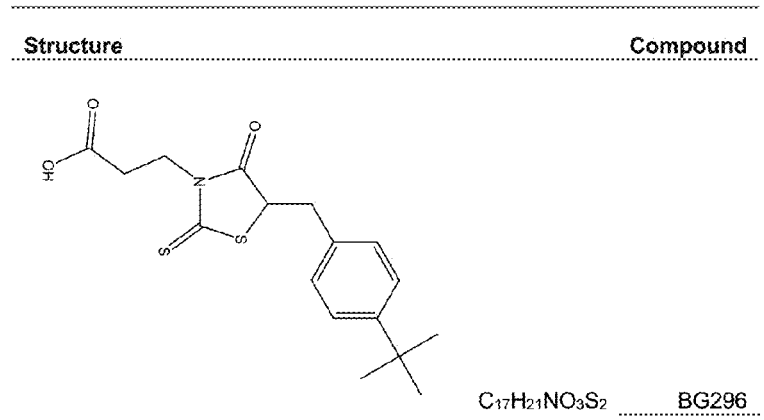

When any variable occurs more than one time in any constituent or in any formula, its definition on each occurrence is independent of its definition at every other occurrence. Thus, for example, a particular group on a compound may include zero to about three $R^{10}$ substituents, then the group may optionally be substituted with up to three $R^{10}$ substituents, and $R^{1o}$ at each occurrence is selected independently from the defined list of possible $R^{10}$ substituents. Also, by way of example, for the group $N(R^{10})(R^{11})$, each of the two substituents on N is independently selected from the defined list of possible $R^{10}$ and $R^{11}$ substituents; if $R^{10}$ is aryl, it may be optionally substituted with one or more additional $R^{10}$ groups. Combinations of substituents and/or variables are permissible only if such combinations result in stable compounds. FIG. 6 illustrates how recursive substituents may be used with respect to substitutions to provide compounds of Formula I.

By "stable compound" or "stable structure" is meant herein a compound that is sufficiently robust to survive isolation to a useful degree of purity from a reaction mixture, and to survive formulation into an efficacious agent, for example, a diagnostic or therapeutic agent.

As to any of the above groups or compounds described herein, which contain one or more substituents, it is understood, of course, that such groups do not contain any substitution or substitution patterns that are sterically impractical and/or synthetically non-feasible. It will be appreciated that the compounds of the invention contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

One diastereomer may display superior activity compared to another. When required, separation of racemic materials can be achieved by high performance liquid chromatography (HPLC) using a chiral column or by a resolution using a resolving agent such as camphonic chloride, as in Thomas J. Tucker et al., *J. Med. Chem.* 1994, 37, 2437-2444. A chiral compound may also be directly synthesized using a chiral catalyst or a chiral ligand; see, for example, Mark A. Huffman, et al., *J. Org. Chem.* 1995, 60, 1590-1594.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in a cell, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 50%, 60%, 80%, 90%, 95%, or 99%, for example, compared to the growth or progression that occurs in the absence of the treatment or contacting.

Methods of Inhibition and Treatment

The compounds described herein have been found to have antiviral activity selective toward flaviviruses. Accordingly, the invention provides compounds having application in the clinical treatment of infection of dengue virus (DV) and other members of flaviviridae, such as West Nile virus (WNV), and Japanese encephalitis virus (JEV). Thus, the invention provides methods for the treatment of viral infections such as Dengue fever (DF) and dengue haemorrhagic fever (DHF)/dengue shock syndrome (DSS).

To date, effective antiviral therapies and vaccines are not yet available to treat or prevent DV and other flavivirus infections. For the control of DV infection, in addition to better insecticides, rapid diagnostics, safe vaccine, the strategic use of antivirals during periods of viremia can be beneficial to reduce the symptoms of the infection, for example, to the point where the body's natural immune system can effectively fight the infection. DHF and DSS are considered to directly correlate with higher titer of viremia, therefore, antivirals that can lower viral load by 2 logs or greater, such as the compounds described herein, can significantly reduce serious dengue diseases, decrease mortality associated with pandemic and slow down transmission.

The compounds described herein as viral inhibiting agents are generally capable of inhibiting viral replication in vitro and/or in vivo. For example, a compound of Formula (I) when contacted with a flavivirus-infected cell can reduce the amount of infectious viral particles produced by the infected cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95%, compared to the number of infectious viral particles produced by a cell not contacted with the inhibiting agent.

A wide variety of methods are available to assess whether a compound can reduce viral load in vitro and/or in vivo. In vitro assay typically determines the number of viral particles present in the culture medium, wherein an in vivo assay typically measures the viral titer present in a bodily fluid of an infected subject. Bodily fluids suitable for viral titer measurement include, but are not limited to, blood, serum, plasma, saliva, semen, spinal fluid, urine, sweat, and cerebral spinal fluid. Commonly employed methods for detecting viral load in vitro or in vivo include quantitative reverse transcriptase polymerase chain reaction (PCR) and branched DNA (bDNA) tests. Numerous quantitative assays for measuring the viral load (titer) of viral RNA have been developed. Many such assays are available commercially, including a quantitative reverse transcription PCR (RT-PCR).

The compounds described herein can also be characterized by their ability to inhibit guanosine triphosphate (GTP)-binding by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95%, compared to the binding in the absence of the compound.

In some embodiments, the inhibiting agents described herein (e.g., compounds of Formula I) inhibit guanosine triphosphate (GTP)-binding with a 50% inhibitory concentration ($IC_{50}$) of about 100 µM to 50 µM, about 50 µM to 25 µM, about 25 µM to 10 µM, about 10 µM to 5 µM, about 5 µM to 1 µM, about 1 µM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, less than about 5 nM, less than about 1 nM, less than about 0.1 nM, or less than about 0.01 nM.

The compounds and pharmaceutical compositions thereof described herein are particularly useful for treating infection by a virus of the Flaviviridae family. In one embodiment, the invention provides a method of treating a subject infected with a virus from the Flaviviridae family comprising administering to the subject the compound of Formula I or a pharmaceutical composition comprising, or consisting essentially of the compound of Formula I, in an amount that is effective in reducing viral load of the virus in a subject.

The treatment methods typically comprise administering to a subject infected with such virus a therapeutically effective amount of an inhibiting agent in one or more doses, alone or in combination with other agents such as ribavarin. For subjects already infected with a virus of the Flaviviridae family such as dengue virus, yellow fever virus, or West Nile virus, the methods described herein are generally effective in reducing the viral load over a period of a few days, a few weeks or a few months. The invention also provides methods of prophylactically treating an infection by a virus of the Flaviviridae family of viruses comprising administering an effective amount of an inhibiting agent described herein to a subject in need thereof.

An inhibiting agent described herein and pharmaceutical composition comprising the agent can be administered to a subject in one or more doses. In an embodiment, the inhibiting agent can be administered in an amount of about 10 mg to 1000 mg per dose, e.g., about 10 mg to 20 mg, about 20 mg to 25 mg, about 25 mg to 50 mg, about 50 mg to 75 mg, about 75 mg to 100 mg, about 100 mg to 125 mg, about 125 mg to 150 mg, about 150 mg to 175 mg, about 175 mg to 200 mg, about 200 mg to 225 mg, about 225 mg to 250 mg, about 250 mg to 300 mg, about 300 mg to 350 mg, about 350 mg to 400 mg, about 400 mg to 450 mg, about 450 mg to 500 mg, about 500 mg to 750 mg, or about 750 mg to 1000 mg per dose.

In some embodiments, the amount of the inhibiting agent per dose is determined on a per body weight basis. For example, the inhibiting agent can be administered in an amount of about 0.5 mg/kg to 100 mg/kg, e.g., about 0.5 mg/kg to 1 mg/kg, about 1 mg/kg to 2 mg/kg, about 2 mg/kg to 3 mg/kg, about 3 mg/kg to 5 mg/kg, about 5 mg/kg to 7 mg/kg, about 7 mg/kg to about 10 mg/kg, about 10 mg/kg to 15 mg/kg, about 15 mg/kg to 20 mg/kg, about 20 mg/kg to 25 mg/kg, about 25 mg/kg to 30 mg/kg, about 30 mg/kg to 40 mg/kg, about 40 mg/kg to 50 mg/kg per dose, about 50 mg/kg to 60 mg/kg, about 60 mg/kg to 70 mg/kg, about 70 mg/kg to 80 mg/kg, about 80 mg/kg to 90 mg/kg, or about 90 mg/kg to 100 mg/kg, or more than about 100 mg/kg.

Those of skill will readily appreciate that dose levels can vary as a function of the specific inhibiting agent administered, the severity of the symptoms and the susceptibility of the subject to side effects. Preferred dosages for a given compound are readily determinable by those of skill in the art by a variety of means.

In some embodiments, multiple doses of the inhibiting agent are administered. The frequency of administration of the inhibiting agent can vary depending on any of a variety of factors, e.g., severity of the symptoms, and the like. For example, in one embodiment, the inhibiting agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). The inhibiting agent may also be administered continuously.

By way of illustration, efficacious dosing of a compound described herein can include dosing at about 200 mg po BID, 150 mg po BID, 75 mg po BID, or 50 mg po BID. The total daily dose can also be split among multiple doses, which allows for a lower dose at each administration with less potential for sedation while maintaining sufficient efficacy. Alternatively, a more frequent dosing schedule can be applied for severe cases, for example, TID administration or administration every 4, 6, 8, or 12 hours of a 25 mg, 50 mg, 75 mg, 150 mg or higher dose. Alternatively, a sustained release formulation may be used.

The duration of administration of the inhibiting agent, e.g., the period of time over which the inhibiting agent is administered, can vary, depending on any of a variety of factors, e.g., patient response, and the like. For example, the inhibiting agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years.

The practice of certain methods described herein can involve administering an effective amount of an inhibiting agent or a pharmaceutical composition comprising such inhibiting agent. The specific dose will vary depending on the particular compounds chosen, the dosing regimen to be followed, whether it is administered in combination with other compounds, timing of administration, the tissue to which it is administered, and the physical delivery system in which it is carried. In an embodiment, an effective amount of the inhibiting agent is an amount that, when administered in one or more doses to a host (e.g., human) in need thereof, reduces viral load in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the viral load in the individual not treated with the inhibiting agent.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR (RT-PCR); and a branched DNA (deoxyribonucleic acid) signal amplification assay.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating a viral infection in a mammal, which involve administering to a mammal having a viral infection an effective amount of a compound or composition described herein. A mammal includes a primate, human, rodent, canine, feline, bovine, ovine, equine, swine, caprine, bovine and the like. A viral infection refers to an invasion of a host, such as a human, particularly a host organism's bodily tissues by a disease-causing virus, such as a flavivirus. The infection can include viral multiplication, and the reaction of host tissues to these viruses and the toxins they produce.

The ability of a compound of the invention to treat a viral infection may be determined by using assays well known to the art. For example, the design of treatment protocols, toxicity evaluation, data analysis, and quantification of inhibition are known, including information referenced herein and described in the examples below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Novel Antiviral Inhibition of the Flavivirus Guanylyltransferase Enzyme

Arthropod-borne flavivirus infection causes serious morbidity and mortality worldwide, but there are currently no effective antiviral chemotherapeutics available for human use. Therefore, it is critical that new therapeutics to virus-specific targets be developed. To identify new compounds that may be used as broadly active flavivirus therapeutics, we have performed a high-throughput screen of 235,456 commercially available compounds for small molecule inhibitors of the dengue virus NS5 RNA capping enzyme. We identified a family of compounds, the 2-thioxothiazolidin-4-ones, which show potent biochemical inhibition of GTP binding and guanylyltransferase function of the capping enzyme. During the course of structure-activity relationship analysis, a molecule within this family (E)-(3-(5-(4-tert-butylbenzylidene)-4-oxo-2-thioxo-1,3-thiazolidin-3-yl)propanoic acid (BG-323)) was found to possess significant antiviral activity in a dengue virus subgenomic replicon assay. Further testing of BG-323 demonstrated that this molecule is able to reduce the replication of infectious West Nile and yellow fever viruses in cell culture with low toxicity. This Example thus identifies the first inhibitors that target the GTP-binding/guanylyltransferase activity of the flavivirus RNA capping enzyme.

Materials and Methods.

Expression and Purification of flavivirus NS5 Capping Enzymes. Recombinant NS5 capping enzyme domains from yellow fever virus (strain 17D, AA 1-268) and dengue virus type 2 (strain 16681, AA 1-267) were previously described (9). Briefly, yellow fever virus capping enzyme was produced in BL21 (DE3) Codon Plus *E. coli* cells (Novagen). Dengue virus capping enzyme was produced in BL21 (DE3) pLysS *E. coli* cells (Novagen). Yellow fever and dengue virus proteins were induced and purified using the same protocol. Cultures (750 mL) were induced with 400 μM IPTG overnight at 22° C., and the bacterial pellets were collected and stored at −80° C. in low imidazole lysis buffer. Frozen pellets were thawed and lysed with a microfluidizer, and the lysate was clarified by centrifugation at 18K RPM in an SS-24 rotor. The histidine-tagged proteins were purified from clarified lysates using a nickel-Sepharose™ column on an AKTA Purifier FPLC system. The eluted protein was concentrated using 10K Amicon Ultra concentrators (Millipore) and buffer exchanged into 400 mM NaCl, 20 mM Tris pH 7.5, 0.02% sodium azide, 20% glycerol, and 5 mM Tris (2-carboxyethyl)phosphine hydrochloride (TCEP-HCl) on a Superdex 200 gel filtration column (Amersham). Purified proteins were concentrated using 10K Amicon Ultra concentrators to 100 μM and the concentrations were determined by the absorbance at 280 nm using extinction coefficients obtained from the ExPASy web site. Isolated proteins were >99% pure as determined from SDS-PAGE and Coomassie blue staining. Purified protein was stored at −80° C. in single-use aliquots.

High-Throughput Screening. High throughput screening was performed at the National Screening Lab (NRSB) located at the Harvard Medical School Longwood campus (ICCB-Longwood Screening Facility). To perform the screen, 500 nM of purified dengue virus capping enzyme was complexed with 10 nM of GTP-Bodipy γ-phosphate labeled analog (Invitrogen, Catalog #G22183) in binding buffer (50 mM Tris-Base (pH 7.5), 0.01% NP40, 2 mM dithiothreitol). The complex (30 μL) was dispensed into low-binding opaque black 384 well plates (Catalog #3654, Corning, Corning N.Y.) using a Matrix WellMate liquid handler (Thermo Fisher Scientific, Waltham, Mass.). One column of 10 μM GTP (final concentration) was used as a positive control on each plate, and one column was treated with dimethyl sulfoxide (DMSO) as a negative control. Screening compounds were added to each plate with an Epson compound transfer robot fitted with a 100 nL 384 pin transfer array. Plates treated with 100 nL of compound (5 mg/mL stock concentrations), were allowed to incubate for 1 hour at 23° C., and total fluorescence and fluorescence polarization signals were then detected on an Envision 2103 Multimode platereader with plate stacker attachment (Perkin Elmer, Waltham, Mass.). Each compound was tested in duplicate. The overall Z' score of the screen was >0.7. Compounds that reduced both total fluorescence and fluorescence polarization signals by greater than 50% were cherry-picked and re-tested on a Victor 3V platereader.

Determination of $K_i$ values. Compounds were obtained from ChemDiv and Hit2Lead. All small molecules were diluted in DMSO to 10 mM and were stored in a −20° C. freezer. All compounds were stored in small aliquots in a desiccator to prevent freeze/thaw cycles. $K_i$ values for each compound were determined based on the equation detailed in (17) using a fluorescence polarization assay as previously described (9, 10). Compounds were tested at least 3 times each, and standard deviations for each $K_i$ value are reported.

Guanylation Inhibition Assay. Capping enzyme protein guanylation was performed as described previously (10). Briefly, 3 μM dengue capping enzyme was incubated with 1 μM GTP-ATTO-680 (Catalog #NU-830-680, Jena Bioscience, Jena, Germany), 500 nM $MgCl_2$, 0.1% NP-40, and 1 μM TCEP. Reactions were treated with compounds at final concentrations of 100 μM, 50 μM, 25 μM, 10 μM, and 2.5 μM or mock DMSO controls for 4 hours at 37° C. At the end of the incubation, samples were quenched with 1 μL of 1 M EDTA and 6× Laemmli buffer was added. Samples were boiled for 15 minutes and resolved on 12% SDS-PAGE gels. The gels were imaged for ATTO-680 signal on a Licor Odyssey UV scanner (Licor, Lincoln, Nebr.), and the gels were then stained with Coomassie blue to verify protein equivalence. Coomassie-stained gels were analyzed using the NIH Image J software package. ATTO-680 signals for experimental samples were normalized for protein concentration as compared to on-gel control samples. Inhibition values were determined using non-linear regression analysis in the Prism Software package (Graphpad Software Inc, La Jolla, Calif.). Average $EC_{50}$ values and standard error of the mean values are reported. Each experiment was performed three times.

Antiviral (Replicon) Assay. BHK cells harboring a stable dengue type 2 virus subgenomic replicon (BHK-pD2hRucPac) expressing Renilla luciferase have been previously described (26). BHK-pD2hRucPac cells were grown in DMEM media supplemented with 10% fetal bovine serum and 3 μg/mL puromycin to maintain stability of the replicon. Working stocks of BHK-pD2hRucPac cells were used for two months and then replaced with fresh stocks to maintain the sensitivity of the replicon to antiviral drugs.

Antiviral assays were performed by seeding white opaque 96-well cell culture plates (Catalog #T-3021-13, Bioexpress, Kaysville, Utah) with 2000 cells/well in 100 μL DMEM supplemented with 10% FBS but without puromycin. Cells were allowed to attach overnight at 37° C. The next day, test compounds were diluted in DMSO and 1 μL of each dilution was added to appropriate wells (200 μM to 78 nM final concentrations). Each plate included a control column of DMSO with no drug and several rows of Ribavirin (200 μM to 78 nM final concentrations) to verify the sensitivity of the replicons to drug. Cells were incubated at 37° C. for 72 hours, when cells were tested for Renilla Luciferase activity and cell viability. Media was replaced with 25 μL of DMEM containing 1:1000 dilution of Viviren Live Cell Renilla Luciferase Reagent (Catalog #E6492, Promega, Madison, Wis.), and the plates were incubated for 10 minutes at 37° C. Renilla Luciferase signal was detected on a Victor Multi-Mode plate reader (Perkin Elmer).

After reading the Renilla Luciferase signal, 25 μL of CellTiter-Glo cell viability reagent (Catalog #G7571, Promega, Madison, Wis.) was added to each well, and the cells were incubated for 10 minutes at 37° C. CellTiter-Glo signal was detected in the same manner as the Viviren signal. Renilla and CellTiter-Glo experimental samples were converted to percent of the averaged on-plate DMSO controls, and non-linear regression curves (variable slope) were generated with the Prism software. $EC_{50}$ values were calculated for Renilla luciferase and $CC_{50}$ values calculated for CellTiter-Glo curves, and averaged values and standard deviations over at least three experiments for each are reported. Therapeutic index (TI) is calculated as $CC_{50}/EC_{50}$.

Viral assays. West Nile virus (Kunjin subtype) and yellow fever (17D) virus growth curves were performed in BHK cells. Cells were plated in 6-well plates at 100,000 cells/well and allowed to attach overnight. The next day cells were treated with BG-323 or DMSO at the indicated concentrations and concurrently infected with Kunjin or yellow fever virus at a multiplicity of infection (MOI) of 0.01. Media samples (250 μL) were taken at 4, 12, 24, 36, 48, 72, 96, and 120 hours post infection and stored at −80° C. Samples were titered for virus concentration by plaque assay on BHK cells as previously described (19). Viral growth curves were generated with Prism (Graphpad Inc., La Jolla, Calif.). Renilla luciferase expressing Sindbis virus pBG451 was previously described (24). Renilla signal was detected in infected BHK cells with Viviren live cell reagent (Promega), and cell viability was detected with CellTiter Glo reagent (Promega). Each experiment was performed three times and the average plaque forming unit (PFU)/mL and standard error of the mean is reported.

Quantitative Reverse Transcriptase Real-Time PCR Analysis. West Nile virus (Kunjin) RNA was extracted from cell culture media with Trizol LS (Invitrogen, La Jolla, Calif.) following the manufacturer's protocol. Quantitative reverse transcriptase real-time PCR reactions for Kunjin genomic RNA were performed using the Brilliant III Ultra-Fast SYBR QRT-PCR Master Mix (Catalog # 600886, Agilent, Santa Clara, Calif.) with primers Fwd 6170 (5'-TGGACGGG-GAATACCGACTTAGAGG (SEQ ID NO: 1)) and Rev 6278 (5'-ACCCCAGCTGCTGCCACCTT (SEQ ID NO: 2)). To set up qRT-PCR reactions, 2 μL of extracted RNA was added to 5 μL of 2× master mix, 1 μL of 5 μM Fwd 6170 primer, 1 μL of 5 μM Rev 6278 primer, and 1 μL of 100 mM DTT in 96-well PCR plates with optically clear sealing films. No RNA and no primer controls were included in each experiment. qRT-PCR reactions were performed on a BioRad CFX384 real-time PCR thermal cycler using the following cycling conditions: Reverse transcriptase step=50° C., 10 minutes; denature step=95° C., 3 minutes; PCR (40 cycles)=95° C., 5 seconds/60° C., 10 seconds. Melt curves were performed at the end of each run, to verify the specificity of the detected SYBR signal. Cq values were determined by setting the threshold to 40 for all experiments. Standard curves were generated from diluted media containing Kunjin virus of known titer (PFU/mL), and the Cq values from experimental samples were compared to the standard curve to establish PFU equivalent/mL values for each sample (y=−3.475x+27.577, y=Cq , X=$Log_{10}$(PFU)). The limit of detection in these experiments was determined to be 10 PFU equivalents/mL. All experiments were performed three times, and the average and standard error of the mean reported.

Western blot analysis. BHK cells were infected with Kunjin virus at MOI=0.1 and treated with increasing concentrations of BG-323 or DMSO. At 72 hours post-infection, cells were collected and lysates were prepared by boiling in 1× laemelli buffer. Lysates were resolved on 12% PAGE gel and protein was transferred to nitrocellulose membranes. Western blot analysis was performed with anti-NS5 antibody 5D4 (12) and anti-β-actin (Abcam #6276) on a separate membrane. Bands were detected with an IR-DYE-800 anti-mouse secondary antibody (Rockland Scientific) on an Odyssey UV Imaging system.

Modeling Analysis. Each molecular structure was drawn using Maestro and minimized using Macromodel (Schrodinger, N.Y.). For minimization of all small molecules, the dielectric constant was set to 4.0 (aqueous), the maximum iterations was set to 1000 and the convergence threshold was set to 0.05 kJ/Å-mol. The OPLS_2005 forcefield was used and conjugate gradient methodology applied.

Docking and scoring. All small molecules were evaluated with GOLD (25) to determine potential orientations of association with dengue virus capping enzyme (PDB Code: 3EVG) and yellow fever virus capping enzyme (PDB Code: 3EVD). Unless discussed below, default parameters were applied. The centroid of the docking sphere is: x=16.37, y=−52.73 and z=17.934, with an active site radius of 10 Å. Each run consisted of 50 iterations per small molecule. The fitness function and search settings had the annealing parameters such that van der waals radii=4 Å and hydrogen bonding distance=2.5 Å. Fifty docked conformations were obtained for each compound and DSViewerPro 5.0 (Accelrys, Calif.) was used to visualize properties between the small molecule and the capping enzyme protein. For the majority of compounds one predominant conformation was obtained and was chosen as the physiologically relevant orientation for further analysis. For compounds with multiple orientations (generally observed for compounds with lower binding affinity), the orientation most similar (via visual inspection) to the conserved physiologically relevant orientation was chosen for further analysis. The docking protocol used was previously validated for ligand binding to the dengue capping enzyme (10) and can recapitulate the association of GTP, GDP, and GMP within the binding site.

Results

High-throughput screening. Based on our previous screen of 46,323 compounds against the yellow fever virus capping enzyme (10), we performed a second screen of the remaining 235,456 compounds in the NRSB library for molecules that were able to displace GTP from the dengue virus capping enzyme. This screen identified 633 compounds that showed >50% inhibition in fluorescence polarization and had a corresponding reduction in total fluorescence intensity, similar to what we have previously reported with our GTP-Bodipy binding assay (9, 10).

The 633 compounds, which were determined to be tractable to medicinal chemistry, were cherry picked from the NSRB libraries and were re-checked for activity using cherry-picked material from the NRSB library on a different platereader. Of the 633 molecules, 222 repeated, a repeat rate of 35.1%. Within this set of 222 compounds we observed a small cluster of compounds with a thioxothiazolidine core and an acid moiety that appeared to displace GTP-Bodipy from the capping enzyme with varying strengths based on relative displacement in the HTS assay (Table 1), indicating that structure activity relationships can be exploited within this family. The thioxothiazolidines were not necessarily the strongest "hits" in the 222 compounds that repeated, but because the thioxothiazolidine core is found in known FDA approved drugs, such as epalrestat, and a number of analogs were commercially available, this family of inhibitors was further evaluated.

TABLE 1

Thioxothiazolidin molecules identified from high-throughput screening.

| Compound | ICCB Library | ICCB Plate | Well | HTS Activity |
|---|---|---|---|---|
| 1013-0252 | ChemDiv1 | 588 | E07 | S |
| 0806-0194 | ChemDiv1 | 587 | P15 | W |
| 5587305 | CBMicro | 765 | F19 | M |
| 2044-5240 | ChemDiv3 | 1475 | P10 | M |

HTS displacement activity: Weak (W)=50%-75% reduction in FP signal; Moderate (M)=76%-90% reduction; Strong (S)=>90% reduction).

Scheme A. Structures of Compounds from Table 1.

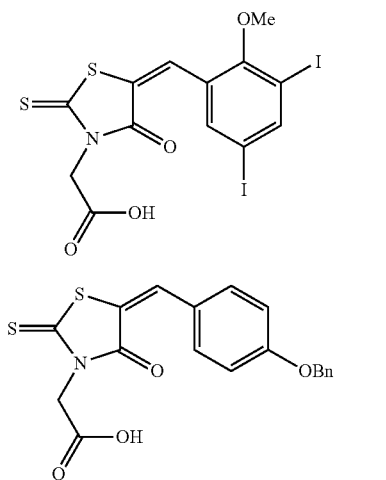

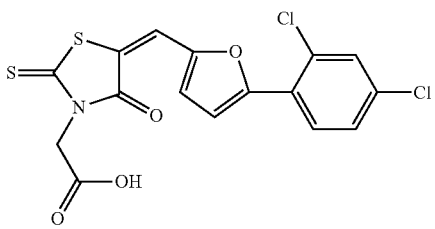

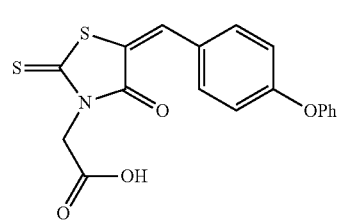

SAR Analysis of the Thioxothiazolidines. The four compounds from Table 1 and Scheme A were ordered in 5 mg quantities from ChemDiv and Hit2Lead. Twenty-one additional commercially available compounds having a core structure of Formula (I) were purchased (see for example, the 2-thioxothiazolidin-4-one BG-5, FIG. 1). $K_i$ values were determined for 24 compounds against dengue and yellow fever virus capping enzyme using 24-point titration curves (9, 10). Compound 2044-5240 caused the protein in the $K_i$ assays to precipitate, and no usable data was obtainable. Otherwise, the thioxothiazolidine-based series of compounds exhibited apparent $K_i$ values ranging from >100 μM to 1.5 μM (Table 2). The substituents of the thioxothiazolidine-based series of compounds cited in Table 2 are based on the structure of Formula I:

TABLE 2

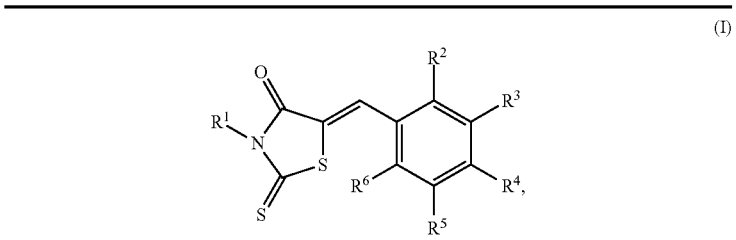

Structure activity relationship analysis of thioxathiazolidines.

| Compound | $R^1$ | $R^2$ | $R^3$ | $R^4$ | $R^5$ | $R^6$ |
|---|---|---|---|---|---|---|
| BG-5 (1013-0252) | $CH_2COOH$ | $OCH_3$ | I | H | I | H |
| BG-115 (5587305) | $CH_2COOH$ | H | H | $OC_6H_5$ | H | H |
| BG-170 (0806-0194) | $CH_2COOH$ | H | H | $OCH_2C_6H_5$ | H | H |
| BG-309 (5629185) | $CH_2COOH$ | $OCH_3$ | H | H | $OCH_3$ | H |
| BG-310 (4670-0432) | $CH_2CH_2COOH$ | $OCH_3$ | H | H | H | H |
| BG-312 (5576225) | $CH_2COOH$ | H | H | $CH(CH_3)_2$ | H | H |
| BG-313 (5875208) | $CH_2COOH$ | OH | Cl | H | Br | H |
| BG-314 (6964247) | $CH_2COOH$ | H | Br | F | H | H |
| BG-315 (5646834) | $CH_2COOH$ | OH | Cl | H | Cl | H |
| BG-317 (5580978) | $CH_2COOH$ | Cl | Cl | H | H | H |
| BG-318 (5567899) | $CH_2COOH$ | H | Cl | Cl | H | H |
| BG-319 (5221260) | $CH_2COOH$ | Cl | H | Cl | H | H |
| BG-320 (67975950) | $CH_2COOH$ | F | H | H | Br | H |
| BG-321 (51403100) | $CH_2CH_2COOH$ | H | H | F | H | H |
| BG-322 (6105937) | $CH_2CH_2COOH$ | H | H | $CH(CH_3)_2$ | H | H |
| BG-323 (7174672) | $CH_2CH_2COOH$ | H | H | $C(CH_3)_3$ | H | H |
| BG-324 (7426520) | $CH_2CH_2COOH$ | Cl | Cl | H | H | H |

TABLE 2-continued

| | | | | | | |
|---|---|---|---|---|---|---|
| BG-325 (5265280) | CH$_2$COOH | H | H | H | H | H |
| BG-327 (5140309) | CH$_2$CH$_2$COOH | H | H | H | H | H |
| BG-328 (5865139) | CH$_2$CH$_2$COOH | H | Cl | Cl | H | H |
| BG-329 (5337317) | CH$_2$CH$_2$COOH | F | H | H | H | H |
| BG-330 (5558800) | CH$_2$CH$_2$COOH | Cl | H | Cl | H | H |
| BG-331 (5558233) | CH$_2$CH$_2$CH$_2$COOH | Cl | H | Cl | H | H |
| BG-332 (6137648) | CH$_2$CH$_2$COOCH$_3$ | Cl | H | Cl | H | H |

| Compound | Dengue Ki (mM) | Dengue SD (mM) | Yellow Fever Ki (mM) | Yellow Fever SD (mM) |
|---|---|---|---|---|
| BG-5 (1013-0252) | 1.5 | 0.55 | 4.6 | 1.6 |
| BG-115 (5587305) | 4 | 1.8 | 7.7 | 0.15 |
| BG-170 (0806-0194) | 2.9 | 1.2 | 4.4 | 1.5 |
| BG-309 (5629185) | >100 | | >100 | |
| BG-310 (4670-0432) | 40 | 2.4 | 44 | 4.2 |
| BG-312 (5576225) | 18 | 5.5 | 17 | 3.7 |
| BG-313 (5875208) | >100 | | >100 | |
| BG-314 (6964247) | 27 | 2.5 | 27 | 3.5 |
| BG-315 (5646834) | >100 | | >100 | |
| BG-317 (5580978) | 27 | 4.3 | 34 | 9.5 |
| BG-318 (5567899) | 11 | 2.2 | 16 | 6.1 |
| BG-319 (5221260) | 24 | 8.1 | 25 | 6 |
| BG-320 (67975950) | 17 | 2.6 | 23 | 6.5 |
| BG-321 (51403100) | >100 | | >100 | |
| BG-322 (6105937) | 12 | 1.3 | 13 | 2.2 |
| BG-323 (7174672) | 7.5 | 1.7 | 9.5 | 3.2 |
| BG-324 (7426520) | 9.9 | 8 | 16 | 3.5 |
| BG-325 (5265280) | >100 | | >100 | |
| BG-327 (5140309) | >100 | | >100 | |
| BG-328 (5865139) | 14 | 3.3 | 12 | 1.4 |
| BG-329 (5537317) | >100 | | >100 | |
| BG-330 (5558800) | 9.8 | 5.6 | 9 | 0.7 |
| BG-331 (5558233) | 15 | 1.3 | 24 | 9 |
| BG-332 (6137648) | >100 | | >100 | |

$K_i$ values for dengue and yellow fever capping enzymes were calculated as previously described (10).

The structures of the small molecules were examined to understand how changes in compound structure relate to compound binding affinity. A number of trends were identified. First, substitution on the aromatic ring (positions $R^2$-$R^6$) appears to be necessary for a small molecule to be able to compete with GTP for the capping enzyme binding site. The aromatic ring of compound BG-327 is not aryl-substituted ($R^2$-$R^6$=H) and shows no ability to displace GTP ($K_i$=>100 µM). The addition of an isopropyl group at $R^4$ (BG-322) results in improved affinity ($K_i$=12 µM) and replacing the $R^4$ isopropyl group of BG-322 with a larger t-butyl group (BG-323) further boosts affinity ($K_i$=7.5 µM). Both BG-115 ($K_i$=4.0 µM) and BG-170 ($K_i$=2.9 µM) provide additional evidence of this trend as both contain bulky groups at position $R^4$. Interestingly, a fluoride atom at $R^4$ is not sufficient for activity (BG-321; $K_i$>100 µM).

Second, while the compounds examined to date do not allow for an exhaustive exploration of the relationship between the position and size of an aromatic ring substituent and binding affinity, the data do provide some clues. BG-317, BG-318 and BG-319 each have two chlorides on the aromatic ring in varying positions. The presence of chlorides at the $R^3$ and $R^4$ positions (BG-318 $K_i$=11 µM) results in increased binding compared to molecules with chlorides in the $R^2$ and $R^3$ or $R^2$ and $R^4$ positions, BG-317 ($K_i$=27 µM) or BG-319 ($K_i$=24 µM) respectively. Additional compounds are under evaluation to determine whether electronegativity or simply hydrophobic contacts are essential for improved affinity.

A final trend indicated by the data is that affinity is affected by the distance between the acid moiety at the $R^1$ position and the thiazolidine ring. For example, BG-317 (1 carbon) and BG-324 (2 carbons) have observed $K_i$s of 27 µM and 9.9 µM respectively. Similar effects were observed with BG-319 (1 carbon; $K_i$=24 µM) and BG-330 (2 carbons; $K_i$=9.8 µM). However, BG-318 (1 carbon; $K_i$=11.3 µM) and BG-328 (2 carbon; $K_i$=13.6 µM) have similar affinities for the enzyme. Elongating $R^1$ to 3 carbons (e.g., a butyric acid substituent) has a negative effect on compound affinity (compare BG-330 (2 carbon linker) to BG-331 (3 carbon linker)) and modifying the propionic acid to methylpropionate ablates activity. Collectively, these data indicate that there is a structural preference for the distance of the acidic group from the thiazolidine core and that the acid moiety plays a role in compound association with the binding site. Interestingly, there is no observed improvement in affinity without substitutions on the aromatic ring (compare BG-325 and BG-327) confirming the necessity of the aromatic substitutions for significant activity for certain structures.

Overall, these results indicate that capping enzyme binding compounds from the thioxothiazolidine-based series require substitution of the aromatic ring ($R^2$-$R^6$) and that an acid group is necessary for inhibition. Furthermore, preliminary information indicates that affinity is sensitive to the distance between the aromatic group and the acid moiety. These data, which are summarized in FIG. 1B, can aid the optimization of this family of compounds as capping enzyme inhibitors.

Inhibition of guanylyltransferase activity. To determine if the thioxothiazolidine molecules interfere with guanylyltransferase activity, we tested the ability of analogs with GTP $K_i$ values less than 10 µM to interfere with the formation of the guanylated intermediate of the dengue virus capping enzyme (Table 3). We observed that the IC$_{50}$ for guanylation inhibition for each compound was roughly equivalent to the GTP displacement $K_i$ value, except in the cases of BG-324 and BG-330, where guanylation inhibition was weakened or strengthened, respectively. Chlorines in the $R^2$ and $R^3$ positions appear to weaken the enzymatic inhibition capacity of BG-324 (IC$_{50}$=155 µM), whereas chlorines in the $R^2$ and $R^4$ position appear to increase enzymatic inhibition ($IC_{50}$=2.6 µM), although the $K_i$ values for BG-324 and BG-330 are identical. How the capping enzyme forms the guanylated intermediate is unknown, as there is no recognizable guanylyltransferase active site motif present in any flavivirus protein (14). Therefore, without understanding how the reaction occurs it is unclear how the presence of chlorines at $R^2/R^3/R^4$ may differentially affect enzymatic activity.

TABLE 3

Guanylation inhibition and dengue replicon antiviral assays.

| | Guanylation $IC_{50}$ (mM) | Guanylation $IC_{50}$ SEM (mM) | Replicon $EC_{50}$ (mM) | Replicon $EC_{50}$ SEM (mM) | Replicon $CC_{50}$ (mM) | Replicon $CC_{50}$ SEM (mM) | Replicon Therapeutic Index (TI) | ClogP |
|---|---|---|---|---|---|---|---|---|
| BG5 | 6.9 | 3.1 | 97.0 | 17.0 | 270.0 | 94.0 | 2.8 | 4.14 |
| BG115 | 8.8 | 4.9 | 58.0 | 1.2 | 74.0 | 4.7 | 1.3 | 3.94 |
| BG170 | 7.8 | 2.4 | 71.0 | 22.5 | 80.0 | 32.3 | 1.1 | 4.01 |
| BG323 | 7.3 | 2.9 | 30.8 | 1.3 | 184.0 | 41.7 | 6.0 | 4.22 |
| BG324 | 155.7 | 56.9 | 8.5 | 2.1 | 12.0 | 2.5 | 1.4 | 3.89 |
| BG330 | 2.6 | 0.1 | 8.7 | 1.2 | 12.0 | 2.0 | 1.4 | 3.89 |

Guanylation inhibition assays and replicon assays were performed as described in the Materials and Methods section above. Therapeutic index was calculated as $CC_{50}/EC_{50}$.

Overall, this data indicates that of the majority of compounds within this group that displace GTP with reasonable $K_i$ values interfere with the enzymatic activity of the capping enzyme to roughly similar extents.

Preliminary antiviral testing of the Thioxothiazolidines. Concurrently with our biochemical SAR analysis of the thioxothiazolidine analogs, we tested the ability of the six compounds that displayed lower than 10 µM $K_i$ values to reduce Renilla luciferase expression from a persistent dengue replicon in BHK cells (26). Renilla luciferase expression in replicon cells treated with decreasing concentrations of the indicated compound was assayed 72 hours after treatment and used to develop $EC_{50}$ curves. We also calculated the $CC_{50}$ of each compound and determined the therapeutic index (TI) of each compound (Table 3). Compound BG-5 showed weak antiviral effect with a TI value of 2.8 ($EC_{50}$=97 µM; $CC_{50}$=270 µM). BG-323 demonstrated a TI of 6, which was higher than the Ribavirin positive control used in the replicon assays (Ribavirin TI=4.1). The $EC_{50}$ value for BG-323 is 30.8 µM and the $CC_{50}$ value is 184 µM, indicating that while BG-323 is more effective at a higher concentration than Ribavirin ($EC_{50}$=12 µM), it is also significantly less toxic than Ribavirin ($CC_{50}$=49 µM).

Figure 2A:
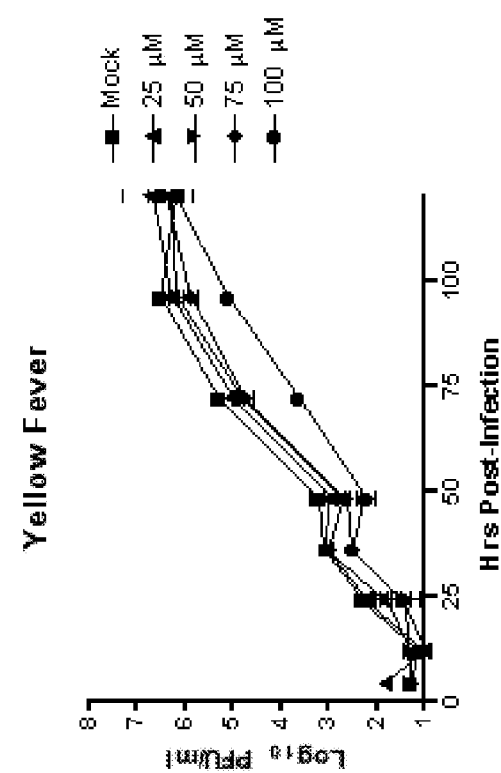
FIG. 2. A) Growth Curve Analysis of Kunjin and Yellow Fever viruses with increasing concentrations of BG-323. Baby hamster kidney cells were infected with Kunjin (FIG. 2A-1) or yellow fever (FIG The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.
Figure 2A:
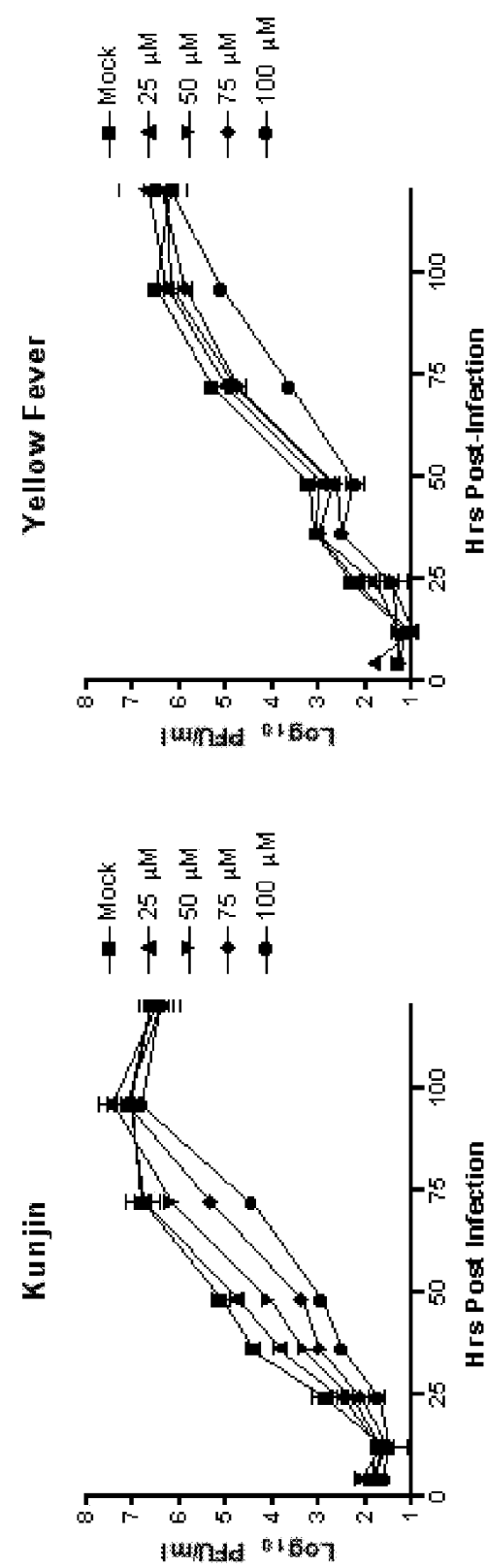
Figure 2B:
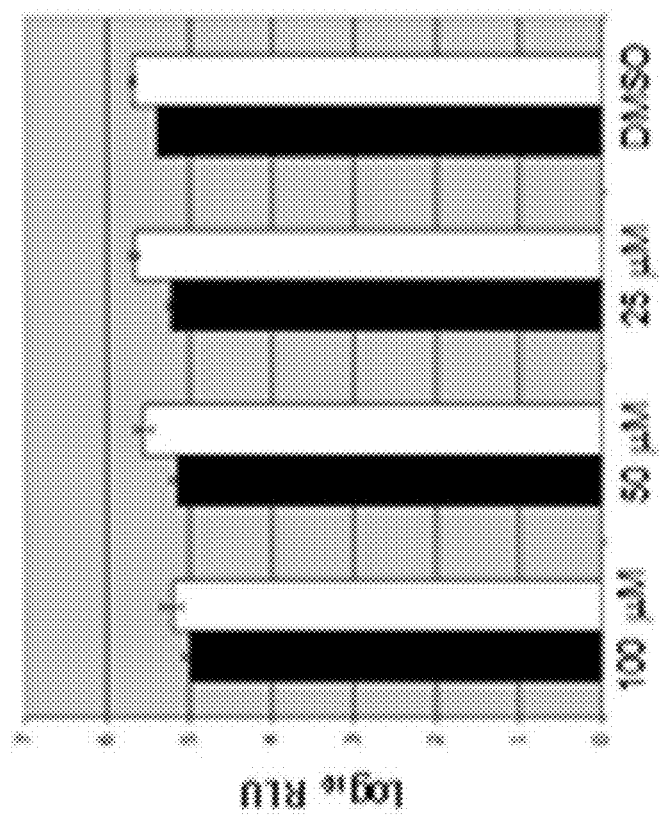

Effects of BG-323 against infectious virus. To test if BG-323 could interfere with the replication of infectious viruses, multi-step growth curves were performed with West Nile (Kunjin) and yellow fever virus in BHK cells with various concentrations of BG-323 added at time of infection (FIG. 2A). The compound BG-323 reduced virus titers by close to 3 logs at several times during Kunjin growth, with a slightly less robust effect also seen with yellow fever virus. The antiviral effect was most pronounced with the highest concentration of BG-323 (100 µM), which is significantly less than its $CC_{50}$ value for BG-323 (184 µM). To determine if BG-323 had activity against non-flaviviruses, BHK cells were treated with BG-323 and the cells were infected with a Sindbis virus that encodes Renilla luciferase (24) for 24 hours. Only a very minor reduction in Renilla signal was observed at the 100 µM concentration of BG-323 with a corresponding minor reduction in cell viability (FIG. 2B). Therefore, BG-323 does not significantly interfere with the replication of a non-flavivirus, thus BG-323 has specificity in inhibiting flavivirus infection.

Figure 3:
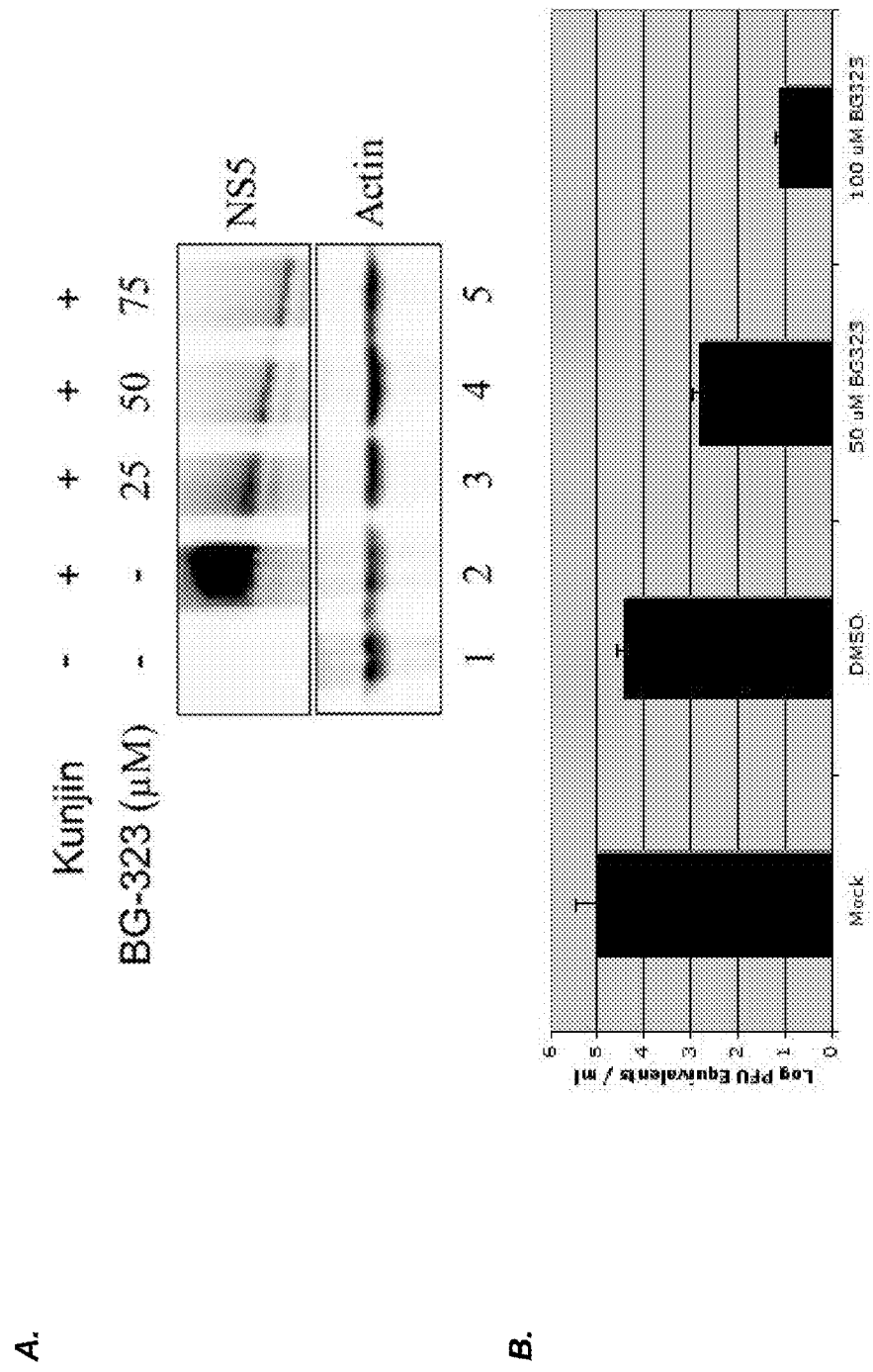

To monitor if BG-323 was affecting viral protein accumulation in infected cells, Kunjin infected cells (MOI=0.01) were treated with increasing concentrations of BG-323 and the cells were assayed for the presence of the viral NS5 protein at 48 hours post-infection by Western blot analysis (FIG. 3A). A significant decrease in NS5 was observed with increasing BG-323 concentrations. A base level of NS5 was present even in high concentrations of BG-323, likely due to translation of the input viral RNA. The significant decrease in NS5 levels indicates that BG-323 can interfere with translation of viral proteins from de novo synthesized genomic RNAs or alter the stability of the translated NS5 protein in infected cells.

To determine if BG-323 was also reducing the amount of viral RNA being released into culture media, BHK cells were infected with Kunjin virus at MOI=0.01 and the cells were treated with DMSO, 50 or 100 µM BG-323, or the cells were mock treated. At 72 hours post-infection, media were collected and viral RNA was extracted, which was used in quantitative real-time reverse-transcriptase PCR reactions. It was observed that DMSO treatment had minimal effects on viral RNA in the media, whereas 50 µM or 100 µM BG-323 significantly reduced the amount of viral RNA detectable in the media (FIG. 3B).

Figure 4:
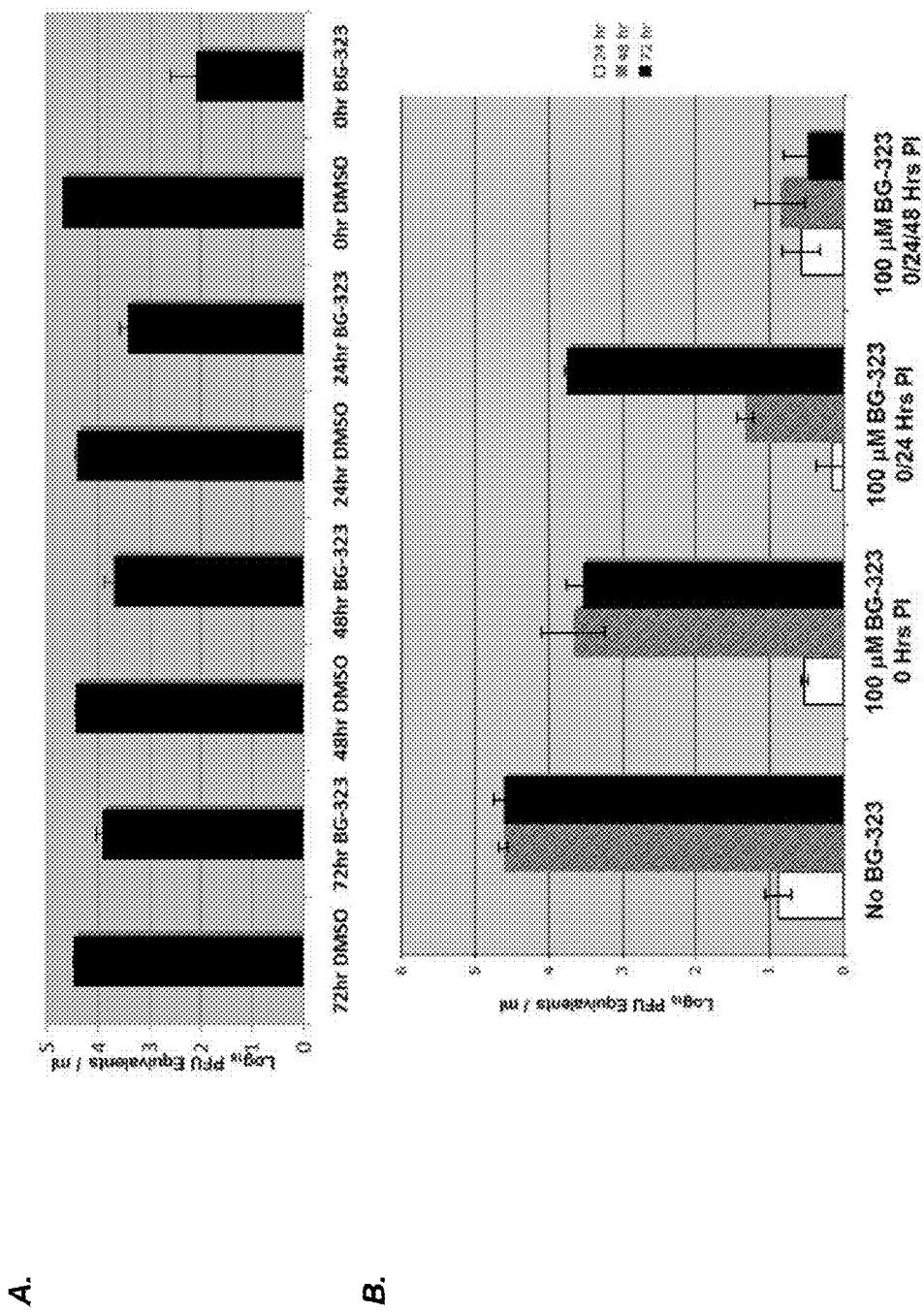

Viral titers of BG-323-treated cultures reached similar levels as mock treated controls at later times during infection, indicating that BG-323 may not be stable throughout the entire time course under the experimental conditions. To assess the activity of BG-323 over time, BG-323 was incubated in media at 37° C. for 3, 2, 1, or 0 days. The pre-incubated media were then added to BHK cells, Kunjin virus was added at MOI=0.01, and media samples were taken 72 hours later. Viral RNA content was determined in media collected from the infected cells by qRT-PCR (FIG. 4A). The amount of viral RNA present in samples with pre-treated media was significantly less than media treated with BG-323 at the time of infection, indicating that BG-323 becomes less active over longer incubation periods.

To determine if replacement of BG-323 during infection could overcome this effect, BG-323 containing media was replaced on Kunjin infected cells every 24 hours for 72 hours and viral RNA in the culture media was monitored at each time point. Adding fresh BG-323 to the cells significantly reduced viral RNA in media over time (FIG. 4B), indicating that the virus remains sensitive to BG-323 and was not becoming resistant to BG-323 over the course of the experiment.

Discussion. This study describes the discovery of a group of novel inhibitors of flavivirus replication that can provide pharmacological benefits for the medical treatment of flaviviruses. A series of compounds able to inhibit an enzyme essential for viral replication has been identified and cell culture activity was shown to be similar to that observed by the known antiviral Ribavirin.

Crystal structures of the capping enzyme with GTP bound have been previously solved (9) and based on mutational studies, GTP association is shown to require π/π stacking interactions with Phe 24 and the formation of hydrogen bonds with Lys 13, Leu 16, Asn 17, Leu 19, Lys 28, Ser 150, Arg 213 and Ser 215. A water bridge also forms between the nitrogenous base and the backbone oxygen of Leu 19, which may play a role in affinity.

Based on the computational docking of BG-5 (FIG. 1A), a compound in this series with high affinity for the enzyme, the thioxothiazolidine family of compounds likely interacts with the enzyme in ways that mimic the association of GTP. Specifically, this compound appears to hydrogen bond with Lys 28 and Ser 150 and π/π stack with the aromatic side chain of Phe 24. In addition, BG-5, GTP and other compounds with improved binding affinity appear to interact with two sub-pockets within the capping enzyme GTP binding site. Sub-pocket 1 allows for interactions between the small molecules and Phe 24 and Lys 21 while sub-pocket 2 allows for interactions between the small molecules and Asn 17 Leu 18, and Leu 19. Interaction with the two sub-pockets provides a rationale for the structure-activity relationships observed in Table 2.

First, compounds with increased bulk in the $R^2$-$R^6$ positions can have increased interactions within one or both of the sub-pockets (for example, BG-322, BG-323). Second, the addition of a carbon-carbon bond linking the acid moiety in the $R^1$ position suggests that these compounds can protrude into these sub-pockets to a greater extent while still maintaining the ability of compounds to form hydrogen bond with Ser 150 and Lys 28. Interestingly, the two sub-pockets also provide a structural explanation for the similar inhibitory effects of BG-318 and BG-328: based on docking studies, both compounds appear to interact with sub-pocket 2 to a similar (sub-optimal) extent and for this reason affinity is not increased by altering the distance between the thiazolidine core and the acid moiety. BG-5 has a high affinity for the capping enzyme and its proposed orientation within the binding site (FIG. 1A) supports the concept that compounds able to interact with either or both sub-pockets result in increases of compound affinity for the binding site. The preliminary pharmacophore shown in FIG. 1B provides a sound basis for providing highly active compounds.

Figure 5:
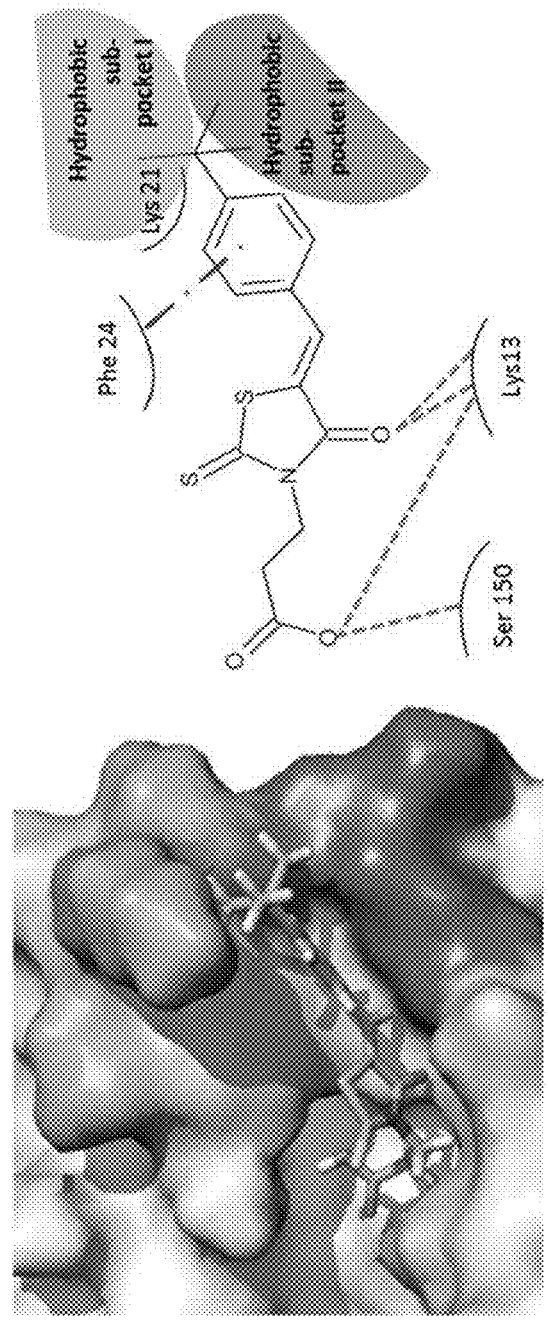

Two compounds within this study, BG-5 and BG-323, displayed highly significant antiviral activity in the dengue virus replicon assay (Table 3). BG-323 displayed a therapeutic index of 6, which is more efficacious than the Ribavirin positive controls. Further testing of BG-323 demonstrated its ability to suppress the replication of West Nile (Kunjin) and yellow fever viruses by plaque assay, qRT-PCR analysis of media samples, and Western blot analysis. These data indicate that BG-323 is able to reduce the amount of infectious virus that is released from infected cells, and indicates that BG-323 has significant antiviral activity in culture. This finding is remarkable as BG-323 (shown docked to the yellow fever capping enzyme in FIG. 5) has a heterocyclic core similar to Epalrestat (22), an FDA approved anti-diabetic drug, indicating that thioxothiazolidines are likely to be clinically viable for the treatment of flavivirus infection.

Thioxothiazolidines are generally considered to be somewhat promiscuous in high-throughput screening assays. However, compounds such as BG-323 demonstrate antiviral activity against flaviviruses but not alphaviruses (FIG. 2B), demonstrating selectivity for flavivirus replication, making it an attractive clinical candidate. Other core structures can be substituted for the thioxothiazolidine core to provide further embodiments of the invention (10).

The biochemical data presented herein demonstrate that compounds of Formula (I) such as BG-323 have activity against the capping enzyme guanylyltransferase activity. Part of the antiviral effect observed in cells may be due to BG-323 interfering with the methyltransferase activity of the capping enzyme or interfering with a cellular protein such as aldose reductase (the target of Epalrestat). BG-323 was also tested to determine if it interferes with other enzymatic assays, such as PCR, but no significant effects were observed, indicating that BG-323 is selective toward flaviviruses and not broadly reactive towards enzymes.

While BG-323 shows significant activity as a novel anti-flaviviral therapeutic, modifications and additional substitutions can provide increased efficacy, such as an increased therapeutic index. BG-323 binds to the capping enzyme with a $K_i$~10 μM and has an $EC_{50}$ value of ~30 μM, indicating that the molecule is able to pass cellular membranes relatively effectively and interfere with viral replication at a concentration not much higher than is inhibitory in the biochemical assays. Therefore, increased binding affinity while maintaining cellular permeability may help lower the effective $EC_{50}$ value of compounds of Formula (I) to increase the therapeutic index for molecules and bring inhibitory activity into even higher therapeutically useful ranges. Accordingly, compounds of Formula (I) such as BG-323 represent a valuable platform of antiviral inhibitors of flavivirus RNA replication.

Citations.
1. Benarroch et al., 2004. A structural basis for the inhibition of the NS5 dengue virus mRNA 2'-O-methyltransferase domain by ribavirin 5'-triphosphate. J Biol Chem 279: 35638-43.
2. Bhattacharya et al., 2009. The flaviviral methyltransferase is a substrate of Caein Kinase 1. Virus Research 141:101-104.
3. Bhattacharya et al., 2008. Phosphorylation of yellow fever virus NS5 alters methyltransferase activity. Virology 380: 276-284.
4. Bollati et al., 2009. Recognition of RNA cap in the Wesselsbron virus NS5 methyltransferase domain: implications for RNA-capping mechanisms in Flavivirus. J Mol Biol 385:140-52.
5. Daffis et al., 2010. 2'-O methylation of the viral mRNA cap evades host restriction by IFIT family members. Nature 468:452-6.
6. Egloff et al., 2007. Structural and functional analysis of methylation and 5'-RNA sequence requirements of short capped RNAs by the methyltrasferase domain of dengue virus NS5. J. of Molecular Biology 372:723-736.
7. Egloff et al., 2002. An RNA cap (nucleoside-2'-O-)-methyltransferase in the flavivirus RNA polymerase NS5: crystal structure and functional characterization. EMBO J 21:2757-68.
8. Geiss et al., 2009. Focus on flaviviruses: current and future drug targets. Future Medicinal Chemistry 1:327-344.
9. Geiss et al., 2009. Analysis of Flavivirus NS5 methyltransferase cap binding. Journal of Molecular Biology 385: 1643-1654.
10. Geiss et al., 2011. A high-throughput screening assay for the identification of flavivirus NS5 capping enzyme GTP-binding inhibitors: implications for antiviral drug development. J Biomol Screen 16:852-61.
11. Guzman et al., 2010. Update on the global spread of dengue. Int J Antimicrob Agents 36 Suppl 1:S40-2.

12. Hall et al., 2009. Monoclonal antibodies to the West Nile virus NS5 protein map to linear and conformational epitopes in the methyltransferase and polymerase domains. J Gen Virol 90:2912-22.
13. Henderson et al., 2011. Analysis of RNA binding by the dengue virus NS5 RNA capping enzyme. PLoS One 6:e25795.
14. Issur et al., 2009. The flavivirus NS5 protein is a true RNA guanylyltransferase that catalyzes a two-step reaction to form the RNA cap structure. RNA 15:2340-2350.
15. Lim et al., 2011. Small molecule inhibitors that selectively block dengue virus methyltransferase. J Biol Chem 286:6233-40.
16. Lindenbach et al., 2007. *Flaviviridae:* the viruses and their replication, p. 1101-1152. In D. M. Knipe, P. M. Howley, D. E. Griffin, R. A. Lamb, M. A. Martin, B. Roizman, and S. E. Straus (ed.), Fields virology, 5th ed, vol. 1. Lippinoctt-Raven Publishers, Philadelphia, Pa.
17. Martin et al., 1991. A simple method for calculating the dissociation constant of a receptor (or enzyme) unlabeled ligand complex from radioligand displacement measurements. Arch Biochem Biophys 284:26-9.
18. Mastrangelo et al., 2007. Structural bases for substrate recognition and activity in Meaban virus nucleoside-2'-O-methyltransferase. Protein Sci 16:1133-45.
19. Paredes et al., 2003. Anti-Sindbis activity of flavanones hesperetin and naringenin. Biol Pharm Bull 26:108-9.
20. Prevention, 2009. Centers for Disease Control and Prevention.
21. Puig-Basagoiti et al., 2009. Identification and characterization of inhibitors of West Nile virus. Antiviral Res 83:71-9.
22. Ramirez and Borja. 2008. Epalrestat: an aldose reductase inhibitor for the treatment of diabetic neuropathy. Pharmacotherapy 28:646-55.
23. Rice et al., 1985. Nucleotide sequence of yellow fever virus: implications for flavivirus gene expression and evolution. Science 229:726-733.
24. Steel et al., 2011. Infectious alphavirus production from a simple plasmid transfection+. Virol J 8:356.
25. Verdonk et al., 2003. Improved protein-ligand docking using GOLD. Proteins 52:609-23.
26. Whitby et al., 2005. Castanospermine, a potent inhibitor of dengue virus infection in vitro and in vivo. J Virol 79:8698-706.
27. Zhou et al., 2007. Structure and function of flavivirus NS5 methyltransferase. J Virol 81:3891-903.
28. Zust et al., 2011. Ribose 2'-O-methylation provides a molecular signature for the distinction of self and non-self mRNA dependent on the RNA sensor MdaS. Nat Immunol 12:137-43.

Example 2

Flavivirus Inhibitors

A variety of flavivirus inhibitors have been identified and evaluated. Examples of specific inhibitors are illustrated in FIG. 6 and select activities are shown below in Table 2-1.

TABLE 2-1

Flavivirus inhibitory activity.

Series1

| Compound | FP_DEN_Ki_AVG_DEN_M | FP_WNV_KI_AVG_WNV_M | FP_YF_KI_AVG_YF_M | Replicon Assay_EC50_M | Replicon Assay_CC50_M | Replicon Assay_TI |
|---|---|---|---|---|---|---|
| BG323 | 7.50E-06 | | 9.50E-06 | 3.08E-05 | 1.84E-04 | 6.0 |
| BG295 | 2.00E-06 | 8.00E-06 | 2.00E-06 | 3.00E-05 | 0.000114 | 3.8 |
| BG297 | 3.00E-06 | | | 7.80E-05 | 8.60E-05 | 1.1 |
| BG21 | 4.20E-05 | | 2.70E-05 | | | |
| BG100 | 3.00E-06 | | 5.00E-06 | 3.70E-05 | 4.90E-05 | 1.34 |
| BG101 | 9.00E-06 | | 8.00E-06 | 4.20E-05 | 4.60E-05 | 1.1 |
| BG114 | 2.00E-06 | | 6.00E-06 | 2.30E-05 | 2.70E-05 | 1.16 |
| BG115 | 4.00E-06 | | 8.00E-06 | 5.80E-05 | 7.40E-05 | 1.27 |
| BG119 | 4.00E-06 | | 5.00E-06 | 4.20E-05 | 5.80E-05 | 1.36 |
| BG120 | 2.00E-06 | | 2.00E-06 | 2.30E-05 | 3.10E-05 | 1.49 |
| BG121 | 3.00E-06 | | 5.00E-06 | 3.30E-05 | 3.90E-05 | 1.2 |
| BG122 | 3.00E-06 | | 5.00E-06 | 4.10E-05 | 5.80E-05 | 1.41 |
| BG123 | 4.00E-06 | | 5.00E-06 | 7.50E-05 | 0.000103 | 1.43 |
| BG124 | 1.40E-05 | | 1.80E-05 | 8.00E-05 | 5.60E-05 | 0.89 |
| BG125 | 2.00E-06 | | 3.00E-06 | 0.000292 | 1.50E-05 | 0.6 |
| BG126 | 1.70E-05 | | 1.90E-05 | 5.20E-05 | 5.10E-05 | 1.02 |
| BG127 | 5.00E-06 | | 6.00E-06 | 0.000109 | 4.00E-05 | 0.7 |
| BG128 | 1.10E-05 | | 1.30E-05 | 4.50E-05 | 4.20E-05 | 1.02 |
| BG129 | 1.10E-05 | | 1.90E-05 | 0.00142 | 4.70E-05 | 0.75 |
| BG130 | 8.00E-06 | | 1.50E-05 | 6.10E-05 | 5.00E-05 | 0.95 |
| BG131 | 6.00E-06 | | 1.20E-05 | 5.40E-05 | 7.10E-05 | 1.56 |
| BG132 | 3.00E-06 | | 3.00E-06 | 0.000114 | 5.00E-05 | 0.82 |
| BG133 | 7.00E-06 | | 1.40E-05 | 0.000126 | 7.70E-05 | 0.87 |
| BG134 | 1.50E-05 | | 1.50E-05 | 6.10E-05 | 6.60E-05 | 1.1 |
| BG135 | 4.00E-06 | | 5.00E-06 | 3.90E-05 | 4.40E-05 | 1.12 |
| BG136 | 1.60E-05 | | 2.70E-05 | 4.10E-05 | 4.90E-05 | 1.21 |
| BG137 | 1.90E-05 | | 2.50E-05 | 5.50E-05 | 6.70E-05 | 1.21 |
| BG138 | 3.00E-06 | | 4.00E-06 | 3.20E-05 | 3.30E-05 | 1.03 |
| BG139 | 5.00E-06 | | 7.00E-06 | 5.10E-05 | 5.60E-05 | 1.11 |
| BG140 | 1.00E-06 | | 2.00E-06 | 1.30E-05 | 2.30E-05 | 1.74 |
| BG141 | 1.00E-06 | | 2.00E-06 | 2.40E-05 | 2.70E-05 | 1.14 |
| BG168 | 2.00E-06 | | 2.00E-06 | 1.30E-05 | 1.20E-05 | 1.17 |
| BG169 | 2.00E-06 | | 2.00E-06 | 2.60E-05 | 2.90E-05 | 1.15 |
| BG170 | 3.00E-06 | | 4.00E-06 | 7.10E-05 | 8.00E-05 | 1.08 |
| BG177 | 1.00E-06 | | 1.00E-06 | 3.00E-05 | 3.00E-05 | 1 |

TABLE 2-1-continued

Flavivirus inhibitory activity.

| | | | | | | |
|---|---|---|---|---|---|---|
| BG177 | | | | 3.00E−05 | 3.00E−05 | 1 |
| BG177 | | | | 2.60E−05 | 3.10E−05 | 1.2 |
| BG179 | 2.00E−06 | | 1.00E−06 | 1.50E−05 | 2.00E−05 | 1.35 |
| BG182 | | | | 8.00E−05 | 9.30E−05 | 1.26 |
| BG182 | 1.80E−05 | | 1.70E−05 | | | |
| BG183 | 1.20E−05 | | 1.30E−05 | | | |
| BG184 | | | | 4.60E−05 | 6.10E−05 | 1.3 |
| BG188 | | | | 5.10E−05 | 5.10E−05 | 1 |
| BG309 | 0.0001 | | | 0.0001 | 0.0001 | |
| BG309 | 0.0001 | | 0.0001 | | | |
| BG310 | 0.000207 | | | 0.0001 | 0.0001 | |
| BG310 | 4.00E−05 | | 4.40E−05 | | | |
| BG311 | 0.000303 | | | 0.0001 | 0.0001 | |
| BG311 | 2.80E−05 | | 3.40E−05 | | | |
| BG222 | 0.0001 | | 0.0001 | | | |
| BG224 | 2.70E−05 | | 2.70E−05 | | | |
| BG225 | 0.0001 | | 0.0001 | | | |
| BG227 | 2.70E−05 | | 3.40E−05 | | | |
| BG228 | 1.10E−05 | | 1.60E−05 | | | |
| BG229 | 2.40E−05 | | 2.50E−05 | | | |
| BG230 | 1.70E−05 | | 2.30E−05 | | | |
| BG265 | 4.60E−05 | | | | | |
| BG273 | 4.00E−06 | | | | | |
| BG274 | 0 | | | 6.30E−05 | 6.00E−05 | 1 |
| BG281 | 2.00E−06 | | | | | |
| BG282 | 1.00E−06 | | | | | |
| BG286 | 0.0001 | | | | | |
| BG289 | 0 | | | 9.20E−05 | 7.90E−05 | 0.9 |
| BG289 | | | | 9.20E−05 | 7.90E−05 | 0.9 |
| BG290 | 0.0001 | | | | | |
| BG291 | 0 | | | 7.50E−05 | 6.80E−05 | 0.9 |
| BG292 | 0.0001 | | | | | |
| BG321 | 0.0001 | | 0.0001 | | | |
| BG324 | 1.00E−05 | | 1.60E−05 | 9.00E−06 | 1.20E−05 | 1.43 |
| BG325 | 0.0001 | | 0.0001 | | | |
| BG326 | 7.70E−05 | | 0.0001 | | | |
| BG327 | 0.0001 | | 0.0001 | | | |
| BG328 | 1.40E−05 | | 1.20E−05 | | | |
| BG329 | 0.0001 | | 0.0001 | | | |
| BG330 | 1.00E−05 | | 9.00E−06 | 9.00E−06 | 1.10E−05 | 1.25 |
| BG331 | 1.50E−05 | | 2.50E−05 | | | |
| BG332 | 0.0001 | | 0.0001 | | | |
| BG333 | 7.00E−06 | | 1.20E−05 | 9.00E−06 | 1.10E−05 | 1.25 |
| BG308 | 2.00E−06 | | 4.00E−06 | 9.70E−05 | 0.000276 | 2.8 |

Series 1b

| Compound | FP_DEN_Ki_AVG_DEN_M | Replicon Assay_EC50_M | FP_YF_KI_AVG_YF_M | Replicon Assay_CC50_M | Replicon Assay_TI |
|---|---|---|---|---|---|
| BG142 | 2.30E−05 | 0.000102 | 5.10E−05 | 0.000137 | 1.43 |
| BG143 | 2.00E−05 | 5.00E−05 | 2.40E−05 | 6.00E−05 | 1.22 |
| BG144 | 2.00E−05 | | 3.80E−05 | | |
| BG145 | 8.00E−06 | | 9.00E−06 | | |
| BG146 | 5.50E−05 | | 6.60E−05 | | |
| BG163 | 5.00E−06 | 3.20E−05 | 9.00E−06 | 3.80E−05 | 1.54 |
| BG166 | 7.00E−06 | 2.80E−05 | 1.40E−05 | 3.30E−05 | 1.2 |
| BG172 | 1.10E−05 | 2.00E−05 | 1.40E−05 | 2.60E−05 | 1.28 |
| BG174 | 6.00E−06 | 5.00E−05 | 6.00E−06 | 5.50E−05 | 1.11 |
| BG175 | 1.30E−05 | 7.80E−05 | 1.70E−05 | 8.20E−05 | 1.39 |
| BG215 | 8.66E−04 | 0.0001 | | 0.0001 | |
| BG226 | 1.00E−04 | | 0.0001 | | |

Series 1c

| Compound | FP_DEN_Ki_AVG_DEN_M | Replicon Assay_EC50_M | Replicon Assay_CC50_M | Replicon Assay_TI |
|---|---|---|---|---|
| BG296 | 1.00E−05 | 0.000167 | 0.000105 | 0.628074 |

Methods for performing the replicon assay are described above in Example 1. The compounds illustrated in FIG. 6 are commercially or otherwise publically available. Other compounds of Formula (I) can be prepared by synthetic techniques, as would be readily recognized by one of skill in the art. Useful synthetic techniques are described by, for example, U.S. Patent Publication Nos. 2013/0090339 (Wang et al.) and 2012/0148534 (Glenn et al.).

Example 3

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |

-continued

| (xi) Topical Cream 2 | wt. % |
|---|---|
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method to inhibit the replication of a flavivirus comprising contacting a flavivirus with an effective inhibitory amount of a compound of Formula (II):

(II)

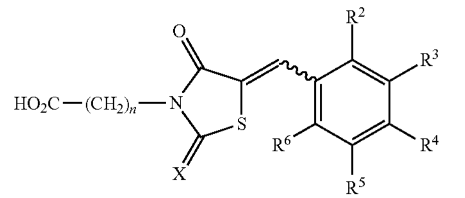

wherein n is 2;

X is S or O;

$R^2$ is H, alkyl, or amino;

$R^3$ is H, alkyl, benzyl, or amino;

$R^4$ is alkyl;

$R^5$ is H, alkyl, benzyl, or amino;

and $R^6$ is H, alkyl, or amino;

or a salt or solvate thereof;

thereby inhibiting the replication of the flavivirus.

2. The method of claim 1 wherein the flavivirus is the dengue virus, the yellow fever virus, or the West Nile virus.

3. The method of claim 2 wherein the flavivirus is in a mammalian host.

4. The method of claim 2 wherein $R^4$ is methyl, ethyl, propyl, iso-propyl, butyl, iso-butyl, sec-butyl, or t-butyl.

5. The method of claim 2 wherein X is S.

6. The method of claim 2 wherein $R^2$ is H, methoxy, hydroxy, or halo, and $R^6$ is H.

7. The method of claim 2 wherein $R^4$ is $(C_3\text{-}C_5)$alkyl.

8. The method of claim 2 wherein $R^3$ and $R^5$ are each independently H, halo, or methoxy.

9. The method of claim 2 wherein X is O.

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tggacgggga ataccgactt agagg 25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
accccagctg ctgccacctt 20

10. The method of claim 2 wherein one or more of $R^3$, $R^4$, and $R^5$ are isopropyl or tent-butyl.

11. The method of claim 1 wherein the compound of Formula (II) is:

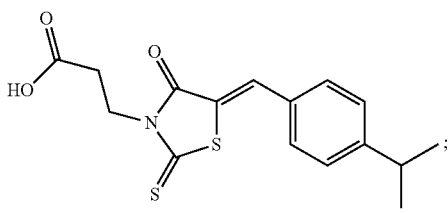
(BG-322)

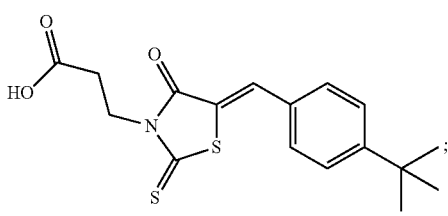
(BG-323)

or a salt or solvate thereof.

12. A method to inhibit the replication of a flavivirus comprising contacting a flavivirus with an effective inhibitory amount of compound BG-323:

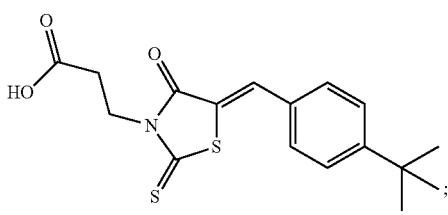
(BG-323)

or a salt or solvate thereof;
thereby inhibiting the replication of the flavivirus.

13. A method of inhibiting the guanosine triphosphate (GTP)-binding and guanylyltransferase activity of a flavivirus RNA capping enzyme comprising contacting the RNA capping enzyme of a flavivirus with an effective inhibitory amount of a compound of Formula (II):

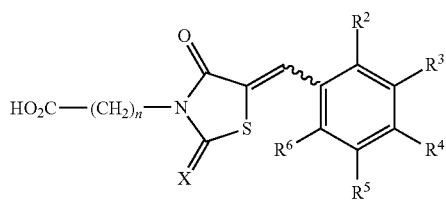
(II)

wherein
n is 1, 2, or 3;
X is S or O;
$R^2$ is H;
$R^3$ is H;
$R^4$ is alkyl;
$R^5$ is H;
$R^6$ is H;
or a salt or solvate thereof
thereby inhibiting the guanosine triphosphate (GTP)-binding and guanylyltransferase activity of the flavivirus RNA capping enzyme.

14. The method of claim 13 wherein the flavivirus RNA capping enzyme is an NS5 capping enzyme.

15. The method of claim 14 wherein the flavivirus RNA capping enzyme is the dengue virus NS5 RNA capping enzyme.

16. The method of claim 13 wherein the compound of Formula (II) has a dengue virus Ki of less than 45 mM.

17. The method of claim 13 wherein the compound of Formula (II) has a yellow fever virus Ki of less than 45 mM.

18. The method of claim 13 wherein the compound of Formula (II) is:

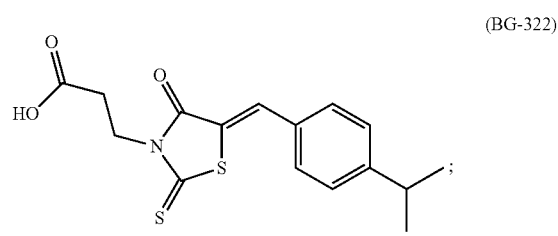 [SMILES: CC(C)(C)c1ccc(/C=C2\SC(=S)N(CCC(=O)O)C2=O)cc1]
(BG-322)

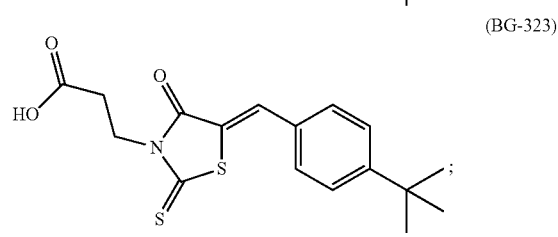
(BG-323)

or a salt or solvate thereof.

19. The method of claim 12 wherein contacting the flavivirus comprises administering a pharmaceutical compositions to a mammal infected with the flavivirus.

20. The method of claim 19 wherein the flavivirus is dengue virus, yellow fever virus, or West Nile virus.

21. The method of claim 20 wherein the pharmaceutical composition further comprises ribavirin.

* * * * *

UNITED STATES PATENT AND TRADEMARK OFFICE
CERTIFICATE OF CORRECTION

| | | |
|---|---|---|
| PATENT NO. | : 9,206,412 B2 | Page 1 of 1 |
| APPLICATION NO. | : 13/907485 | |
| DATED | : December 8, 2015 | |
| INVENTOR(S) | : Brian J. Geiss et al. | |

It is certified that error appears in the above-identified patent and that said Letters Patent is hereby corrected as shown below:

In the Claims

Claim 10, at column 41, line 2:
delete "tent-butyl" and insert -- tert-butyl -- therefor.

Claim 19, at column 42, line 52:
delete "compositions" and insert -- composition -- therefor.

Signed and Sealed this
Twenty-sixth Day of April, 2016

Michelle K. Lee
*Director of the United States Patent and Trademark Office*